US009486486B2

(12) United States Patent
Castex-Rizzi et al.

(10) Patent No.: US 9,486,486 B2
(45) Date of Patent: *Nov. 8, 2016

(54) BACTERIUM AND EXTRACTS OF SAID BACTERIUM AND THE USE OF SAME IN THERAPY

(75) Inventors: Nathalie Castex-Rizzi, Colomiers (FR); Thien Nguyen, Rouffiac-Tolosan (FR); Christine Libon, Castanet-Tolosan (FR); Bertrand Chol, Villy le Pelloux (FR)

(73) Assignees: PIERRE FABRE DERMO-COSMETIQUE, Boulogne-Billancourt (FR); PIERRE FABRE MEDICAMENT, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/997,022

(22) PCT Filed: Dec. 22, 2011

(86) PCT No.: PCT/EP2011/073749
§ 371 (c)(1),
(2), (4) Date: Jul. 16, 2013

(87) PCT Pub. No.: WO2012/085183
PCT Pub. Date: Jun. 28, 2012

(65) Prior Publication Data
US 2013/0296222 A1 Nov. 7, 2013

(30) Foreign Application Priority Data
Dec. 22, 2010 (FR) ...................... 10 61082

(51) Int. Cl.
| | | |
|---|---|---|
| C12N 1/20 | (2006.01) |
| A61K 35/74 | (2015.01) |
| A61K 39/095 | (2006.01) |
| C07K 14/22 | (2006.01) |
| C12R 1/01 | (2006.01) |
| A61K 39/00 | (2006.01) |

(52) U.S. Cl.
CPC ............. *A61K 35/74* (2013.01); *A61K 39/095* (2013.01); *C07K 14/22* (2013.01); *C12N 1/20* (2013.01); *C12R 1/01* (2013.01); *A61K 2039/55594* (2013.01)

(58) Field of Classification Search
None
See application file for complete search history.

(56) References Cited

U.S. PATENT DOCUMENTS

2009/0028805 A1    1/2009  Gueniche et al.

FOREIGN PATENT DOCUMENTS

| EP | 2018891 A1 | 1/2009 |
|---|---|---|
| WO | WO 2005/025614 A2 | 3/2005 |
| WO | WO 2005/030133 A2 | 4/2005 |
| WO | WO 2009/130618 A2 | 10/2009 |
| WO | WO 2009/132244 A1 | 10/2009 |
| WO | WO 2009132244 A1 * | 10/2009 |
| WO | WO 2010/050903 A1 | 5/2010 |
| WO | WO 2010/135704 A2 | 11/2010 |

OTHER PUBLICATIONS

Abraham et al., "Expression of Protease-activated Receptor-2 by Osteoblasts", Bone, vol. 26, No. 1, Jan. 7-14, 2000, pp. 7-14.
Abraham et al., "Inflammatory Bowel Disease", N Engl J Med, vol. 361, No. 21, Nov. 19, 2009, pp. 2066-2078.
Andersen-Nissen et al., "Evasion of Toll-like receptor 5 by flagellated bacteria", PNAS, vol. 102, No. 26, Jun. 28, 2005, pp. 9247-9252, XP002649208.
Arijs et al., "Mucosal Gene Expression of Antimicrobial Peptides in Inflammatory Bowel Disease Before and After First Infliximab Treatment", Plos One, vol. 4, Iss. 11, Nov. 2009, e7984, 10 pages provided.
Cenac et al., "Induction of Intestinal Inflammation in Mouse by Activation of Proteinase-Activated Receptor-2", American Journal of Pathology, vol. 161, No. 5, Nov. 2002, pp. 1903-1915.
Gläser et al., "The Antimicrobial Protein Psoriasin (S100A7) Is Upregulated in Atopic Dermatitis and after Experimental Skin Barrier Disruption", Journal of Investigative Dermatology, vol. 129, 2009, pp. 641-649.
Guéniche et al., "Improvement of atopic dermatitis skin symptoms by Vitreoscilla filiformis bacterial extract", Eur J Dermatol, vol. 16, No. 4, 2006, pp. 380-384.
Hayashi et al., "The innate immune response to bacterial flagellin is mediated by Toll-like receptor 5", Nature, vol. 410, Apr. 26, 2001, pp. 1099-1103, XP002971120.
Hill et al., "Intestinal Bacteria and the Regulation of Immune Cell Homeostasis", Annu. Rev. Immunol., vol. 28, 2010, pp. 623-670 (47 pages provided).
Holzhausen et al., "Protease-Activated Receptor-2 Activation a Major Role in the Pathogenesis of Porphyromonas gingivalis Infection", American Journal of Pathology, vol. 168, No. 4, Apr. 2006, pp. 1189-1199.
International Search Report and Written Opinion of the International Searching Authority for International Application No. PCT/EP2011/073749 dated Mar. 26, 2012 (Forms PCT/ISA/220, PCT/ISA/210, and PCT/ISA/237).
Kaser et al., "Inflammatory Bowel Disease", Annu. Rev. Immunol., vol. 28, 2010, pp. 573-621.
Lourbakos et al., "Arginine-Specific Protease from Porphyromonas gingivalis Activates Protease-Activated Receptors on Human Oral Epithelial Cells and Induces Interleukin-6 Secretion", Infection and Immunity, vol. 69, No. 8, Aug. 2001, pp. 5121-5130.
Needleman et al., "A General Method Applicable to the Search for Similarities in the Amino Acid Sequence of Two Proteins", J. Mol. Biol., vol. 48, 1970, pp. 443-453.

(Continued)

*Primary Examiner* — Anne Gussow
*Assistant Examiner* — Mindy G Brown
(74) *Attorney, Agent, or Firm* — Birch, Stewart, Kolasch & Birch, LLP

(57) ABSTRACT

The present invention relates to a novel bacterial strain isolated and characterized from groundwater. The invention also relates to bacterial extracts and to the therapeutic use of same, notably in the context of the treatment of inflammations.

15 Claims, 10 Drawing Sheets

(56) References Cited

OTHER PUBLICATIONS

Pearson et al., "Improved tools for biological sequence comparison", Proc. Natl. Acad. Sci., vol. 85, Apr. 1988, pp. 2444-2448.

Sambrook et al., "Molecular Cloning: A Laboratory Manual", Cold Spring Harbor Laboratory Press, Third Edition, vol. 3, 2001, pp. 15.40-15.43.

Smith et al., "Comparison of Biosequences", Advances in Applied Mathematics, vol. 2, 1981, pp. 482-489.

Smith et al., "Toll-like receptor 5 recognizes a conserved site on flagellin required for protofilament formation and bacterial motility", Nature Immunology, vol. 4, No. 12, Dec. 2003, pp. 1247-1253, XP002999619.

Tatusova et al., "BLAST 2 Sequences, a new tool for comparing protein and nucleotide sequences", FEMS Microbiology Letters, vol. 174, 1999, pp. 247-250.

Vergnolle, "Clinical Relevance of Proteinase Activated Receptors (PARS) in the Gut", Gut, vol. 54, 2005, pp. 867-874.

Vergnolle, "Protease-activated receptors as drug targets in inflammation and pain", Pharmacology & Therapeutics, vol. 123, 2009, pp. 292-309.

\* cited by examiner

SEQUENCE LISTING

```
<160> NUMBER OF SEQ ID NOS: 10

<210> SEQ ID NO 1
<211> LENGTH: 1487
<212> TYPE: DNA
<213> ORGANISM: Artificial Sequence
<220> FEATURE:
<223> OTHER INFORMATION: Novel bacteria LMB64, belonging to the class of
      Betaproteobacteria, from groudwater
```

-continued

```
<400> SEQUENCE: 1
agtttgatca tggctcagat tgaacgcggg cggcatgctt tacacatgca agtcgaacgg      60
cagcacgggc ttcggcctgg tggcgagtgg cgaacgggtg agtaatgcgt cggaacgcgc     120
cgagtagtgg gggataacgc agcgaaagct gtgctaatac cgcatacgta ctgaggtaga     180
aagtggggga ccttcgggcc tcacgctatt cgagcggccg acgtctgatt agctagttgg     240
tggggtaaag gccccaccaag cgacgatca gtagcgggtc tgagaggatg atccgccaca     300
ctgggactga gacacggccc agactcctac gggaggcagc agtggggaat tttggacaat     360
gggcgcaagc ctgatccagc catgccgcgt gtctgaagaa ggccttcggg ttgtaaagga     420
cttttgtccg ggagcaaagc ctgcttgtta ataccgagtg gggatgagag taccggaaga     480
ataagcaccg gctaactacg tgccagcagc cgcggtaata cgtagggtgc aagcgttaat     540
cggaattact gggcgtaaag cgtgcgcagg cggttgtgca agtctgatgt gaaagccccg     600
ggctcaacct gggaacggca ttggagactg cacggctaga gtgcgtcaga gggggtaga     660 attccacgtg tagcagtgaa atgcgtagag atgtggagga ataccgatgg cgaaggcagc     720
cccctgggat gacactgacg ctcatgcacg aaagcgtggg gagcaaacag gattagatac     780
cctggtagtc cacgccctaa acgatgtcaa ttagctgttg ggggtttgaa tccttggtag     840
cgaagctaac gcgtgaaatt gaccgcctgg ggagtacggc cgcaaggtta aaactcaaag     900
gaattgacgg ggacccgcac aagcggtgga tgatgtggat taattcgatg caacgcgaaa     960
aaccttacct gctcttgaca tgtaccgaag cctgaagaga tttgggtgtg cccgaaaggg    1020
agcggtaaca caggtgctgc atggctgtcg tcagctcgtg tcgtgagatg ttgggttaag    1080
tcccgcaacg agcgcaaccc ttgtcattag ttgccatcat ttggttgggc actctaatga    1140
gactgccggt gacaaaccgg aggaaggtgg ggatgacgtc aagtcctcat ggcccttatg    1200
agcagggctt cacacgtcat acaatggtcg gtacagaggg tcgccaagcc gcgaggtgga    1260
gccaatctca gaaagccgat cgtagtccgg atcgcactct gcaactcgag tgcgtgaagt    1320
cggaatcgct agtaatcgca gatcagcatg ctgcggtgaa tacgttcccg ggtcttgtac    1380
acaccgcccg tcacaccatg ggagtggggg ataccagaag tgggtaggct aaccgcaagg    1440
gaggccgctt accacggtat gcttcatgac tggggtgaag tcgtaac              1487
```

<210> SEQ ID NO 2
<211> LENGTH: 10948
<212> TYPE: DNA
<213> ORGANISM: Artificial Sequence
<220> FEATURE:
<223> OTHER INFORMATION: Novel bacteria LMB64, belonging to the class of
      Betaproteobacteria, from groudwater

```
<400> SEQUENCE: 2
gggcgcagca ccatcgccca ggccaaaagc cacccgtgcc gattcggcgg cctgttgctc      60
gcgctcaatg cgctgcgcct ggtcggccaa gtcggcggct tgctgctcgg ccttgccgc     120 cagggtgtca cgctcgcggg tcagttccgc cacctgctcg gctagggcat cgcgctcggc     180
ctcgatcacc tcaccagcgg ccgccagctc ggcggcttcg ctctgcgcct ggaccaagcg     240
gccctcgacc tcgcgcggg cctgggcggc tgcgcgctcg atctcggcgg caatggcggc     300
ggtcaatgcc tggggcagtt ccggcgcagc agcagcggcc accggccggg cctctcgcca     360
ggcagttaga tgcttgtgaa cggtattcgg gctgccggtg cccaaacgct cgcggatcgc     420
gcggatagtc ggctgctgcc cttcgccgac cagcgcatca gcggcggcgg cgaacgggtg     480
```

```
gcccgtgcag aggcccgcgt cgagcagatc gagcagcagg ccgccaaggc ggcacaggcc    540
cacgaagaag cccgcgccgc cgccacgcag gaagcccggc aagtgcaagc cgaacgcgac    600
gaagcccgca aggtggccgc cgaggcgcgc gagcagaccg cgcgcctggc tgggcaactc    660
gaagccctca ccgcgaagga gcgaaaagcc gatgaaagac cgtgaccaca acgaagcgat    720
ggccggcatg tttcaggccg accccgatt tgccgccgac tatctgcgcc aggtgttggc    780
cgatggcgag cctaccgacg tgcgcgccgg cttgcggcaa atggcggatg tgctgcgcgt    840
cagtcaggcc gccgcgccga ccgattctgc gccttcggcg ggcctctttg accgggccgg    900
cgtgcgctac gaagtggcgt gcgatgtgat cggggcgttg attgcccatt acgccgaaat    960
catgggacgg gaacgcgagc aggcgcagcc gaatgaggcg gttttgcgcg tggccggagc   1020
catgaaggcg gcgctggccg gggagcggga tgatctcgat ccgcgcgata cgcgcggcat   1080
cgaggcggcg atttcgcgct atgcgccact ggcgcgccgg ctgtatggcc aggctgaaaa   1140
cgaccacgcc cgccaggaac agcgtcgcgc cgatttcgac caggtgcatg cttcgctggc   1200
cttggagggg ctggccatga gcgcggacga tttggcggtt caggcgctgc tgatccgggg   1260
cgacattacc cacgatgagg cggtgcagtg ctaccgcatc ctgcatcgcc atgcgcggta   1320
aaaccgactg gccgccgag gtggccggtg tgctgggttt gctcgaatcg cagccgccag   1380
aggcggcgat gctggtgggc tgttttctgg cggcggtagc ccatcccgat catgcggccg   1440
aattggcgat gttcgacaaa ttgccgccag cggcccggat ggtcgtcggg cgattttttcc   1500 tcgttttttct ggcgggcggc ctggacgatg ccgggcgcga aaaactgcat tcgcacatgc   1560
aggcatggtt tgtccgtcag cgccgttttc ggtgaatggc ttgcctcatc cactagggcc   1620
gggcaagggg tgaacagcgg gcgatgctgg cttgcgggac gaccccgcac ccccggaaaa   1680
cttgtcacac accacgcaac tcccgttgct tcgctaaaag ccttgtgccg caaggctttt   1740
agcgaggcga caccgaagac acatcgcggc gacaccgaaa gggccgaacc ggcctaaaac   1800
ccttgctgcg caaggagaac agccgcgctt tcgcgcgcga aagtgcttca aatgcctgtc   1860
ggcatcagca gggtatggat cggcacgccg aaggcgttgg cgatgcgctc caggttgtcc   1920
aaggagatgt ttctgacttg gcgctcgcag tgcgcaacga aggtgcgatg taggccgcac   1980
tcaaaggcga gcgcttcttg tgaccagcct ctttcccggc gtaatcggat catgttggcc   2040
gcgagcacgg cccgcgcgga atgcgcggtt ggtgcgggag gttgagcggc gggagacatg   2100
caaaccagtc tcctgatatg ccgcttttac gtcagccgtg tttaagtcac aatatggttt   2160
tctcatagag aaagacggcg tgacgatggg cagaaaaaca gcaatcaggc gaggggtgc   2220 cgtgttggcc agcctgttga tttgcgcaat tgaaccggtc ggcgcggcct ccctggtcgg   2280
cggtcaaacc gatgattccg tgtgcgacct gggcagcgcg ccacagaacg cccggaagct   2340
gtcggcagcg ggcgacttca tccgcgcgca gtgcaaaaac ggtcaaatgt tggtgggttc   2400
cggcatcgtg cctgccggcg ggtttgactc ggaagtggtg cgcctggcgc gcaccttctg   2460
ccgcatggcg gacattcaga ctcggcgcac gcagggcaac atggccggcc tcgtcatgga   2520
gatcgacgag gtacggtgca tcatcgggaa gttgccgaca tgagaaaagc gatgttggct   2580
ggctttctgg ccgttgtggt ggccaacgtg gttgccgctg agggcggtgc gcccttgcgc   2640
ggcggtgttt gcatcggacc gttccgtggc gctgattccg tcgtgcactg cgagcacatc   2700
ggcaaggtga cgatccgcca gatttacgaa aagggctttc gggtcgttca catgcaggac   2760
gacaagaaca cagccagcta cgttgtgctg gttatcgagg agcaggcgcg atgagggcga   2820
aagcgtggcg gatgctgttt gccgggcggc gctgggtgct ctggcttccc gtgccggcgt   2880
```

```
cggtatggct ggcactgccc gaatggcagc acattcccgc catgttgttg ggcggcctga    2940
tcgtgtggat tcccttctgg ctcgcgtggt ggctcagtga tggcttcgcg ggcatgtcca    3000
ggtggccagg aaccggcgca cctgcggtat ctggcggggt gaacccgcac accggcaagc    3060
catgcacggt gtatcaccag ccgtggggag ataccttcgt gggtggagac tgattatttg    3120
attgaggaac gatgacaagg gccagcaaca agctggccct tgtcgttttc tggactgttt    3180
tacccacaac atccgctctg ctgctgaatt ggcggacatg gcaccgagcc gaacgaacag    3240
aacacgcagc aatccccccgg cttggggcgc agcagcgtat ggcaggccgg gcactcgtag    3300
tagaactggc aggcgtccgt gggcatggtt tcctgctgtg cgtggccgca gtgcgggcag    3360
gtcagcacgg attcgagaat gacggcgctc atcgtggcgt tacctctgca cggtggacgg    3420
atagcctgcg ttcgtcgttg ccgaggtcaa cgcttccggc ttggccttgt cggcgtcata    3480
ggtgacggtg ccgttttctt tgtcgaaatc gaccttgacg gcgctcacac cgggcacttt    3540
ctccagcgac ttcttgactg tgatcgggca tagctcgcag gtcatgttct gaacggccag    3600
cgtgacggtt ttcggggtgg cggccagcac ggcgagcggc acggcagcca gcagagcaat    3660
cagcagtttg cgcatgggag tctcctttca atagaacagc ggggcgaacc acggcacggc    3720
caacagggca agcaacagca cagtgacgat ccagaacgtc aggcgctgcc gctggcgtgt    3780
gcgcggatca gcgcatggcg tgccgggcgt gcagacctgc ggcaccagat agagcttgcg    3840
gaaggccagt ccgagaaaga gcagcgtcat gccgatgaaa aagggccggt acggctccat    3900
cgcggtcagg ctgccaaccc atgagccacc aatgccaagc accagcagga caagcggccc    3960
gacacagcac accgacgcgc cgatggcggt cagtacgctc acgatcaacg agcttttttc    4020
agtgagtcgt gccatgtcgc tttccttgta cctgtttgcc caagtgttac tctaaatccc    4080
gtacctaagt acgagtcaa gggggtgtga tgggaacaga actgaccatc ggcaagctgg    4140
ctgacgctgc cggggtgaat atcgagacga ttcgctacta ccagcggcgc ggcctgctgg    4200
atgagccgcc taaccgcca gggggggcatc ggcgctatgc gcctgagcag gcaaaacgtg    4260
tgcgatttat caagcgggca caggcgcttg gtttcacgct ggacgaggta ggcgcgctac    4320
tgaccctgga tgcggcctgc gcctgcggtg agacgcgagc gctggctgtg cgcaagctgg    4380
gtctgatcga gcagaagatg gctgacctcg cggccatgcg gcaggcgctg ggtggattgg    4440
tgcagcagtg tgatgcgggc gacggtggag ccagctgtcc catcatcgac gtgctggcag    4500
gtaattagat gtgttcaaaa aatggtggtt ttctggacac atgccggttt gccctgtcct    4560
gagttgtcct gatgcgttaa agtgttcatt tattcgttca gctttcaatg tggcggaact    4620
gttcatgaat caacgcatcg gctatgcccg cgtttcgacc gacgaccaaa acctagacct    4680
gcaacgggac gcactccggc aggctggatg ctcaaccatt tacgaggaag cagccagcgg    4740
aaagagcgca gcaaggcccg agcttgagca gtgtcggaag gctctccggc ccggcgacac    4800
gcttgtggtg tggcggcttg atcgccttgg gcgcagcctg cccgacctgg tgcagatcgt    4860
ggctgatctt gaacagcgcg gcgtgcattt cgagagcctg accgagaaga tcgagacggg    4920
gagcgcagcg ggtaagctgc aattccatgt tttcgctgca ctcgccgagt tcgagcgcgg    4980
cctgatccgg gagcgaaccc gggcagggct ggatgcagct cgcgcccgtg gccgatccgg    5040
tggacgcaaa ccgaagctgg acgccaagca gatacgccac attaaggcgc tactacgtga    5100
cccgaatacc tgtgttgctg aactcgcccg tgactacggc gtgtcgagaa caactatcta    5160
taaacactgc ggtgtggttc tgccgcgtac agccgatgaa ggggcaatat gacaaaaaag    5220
```

```
acaacagcat tcgatgtatt cgagaaatgc gtccaagcag ttcaggctgg tgaactgatc    5280
gaatccgttt ctgcgaagga caaggaattc catttccaga actggtttca gaagcgcctc    5340
cagagcctgt cgatgcactt cgaggggtcg ggtcgcaaca cctacccgga cttctgcttg    5400
gtagagcaca ccgagggcta cgagatcaag ggtttggcat ggcctggccg cgagcgcgac    5460
tacgactcga acagccaagt gccgactggc tatcacaacg gccgtcaaat cttctacgtg    5520
ttcgggcgct accccgcaga cctgtctggc tatgccgatc agggcaacgg ccgcaggcag    5580
tacccggtgg ttgacctcgt ggtctgccac ggcgacttcc tcaacgccga tcacaactac    5640
gtccataaga acaagagcgt aaagggcttt ggcacctacg gcgacatcat gatccgcgac    5700
cggaagatgt acgtcgcgcc gacgccattt gcgctgaccg aaggcaccac tggcctgatg    5760
actttgatcc tgccggagaa cttcggcacc gatgaccgtt accaggtggt cggtaacctc    5820
actcgcgtcg aggcggaaac gctggtggtt ggctacaact tgacctgcg cacgaacgag    5880 ctgagcgcag agcgcgtgcc caatcccaac gcaggcaccc agcaccgatt cgtggcctac    5940
cggctcaagg atcaagcgag caagcctgtc tccatgactg gcacccaggt gcagcccgac    6000
gagaacaacc tgccggacga cgaatgaaca ccatcaccga caagatcggg ttcgcttacc    6060
cggttgcagc gaccgcgctg gagtgcgact cccgctggt cgaaatcagc cagatcgccg    6120
agcaggaaag ttggcgaaag gagatcaaca ggccgatcta ccacatccac aagtggtggg    6180
cgaccagact gggtcggtg tttcgtggca ttacccttgg tgctttgagt cagcctggta    6240
ctgacctctg ggcgcagttc tacaaaacgc acgacctggc cggtaaggta gtgctcgatc    6300
ccttcatggg cagtggcacg acgcttggcg aggccgtcaa gctgggtgcc aaggccatcg    6360
gctgcgacat caacccagtc agtaccttcc tcgtacgtca ggcgttcacg ccggcgtccg    6420
aggcagagct gcgtgccgct ttcgagcggc tggaacgtga cgtggcaccg agattcggc    6480 gctactacca gacgcgcgat cctaagacgg gcgagctgat tcaggtcttg tactacttct    6540
gggtcaagac ggtgacgacg cccgagggcg aggtaatccc cttgctgtcg cgctacgtgt    6600
tttcacaaga cgcctacccg aagaagaagc gcgagcgca gatcgtgtgc cctggctgct    6660
ggagtgtgct ggaggatcgc tacgatgcga ctgacctgca ctgccagcac tgcggccacc    6720
agttcaatcc gcaggaaggc ccggccgctg gtcagtacgt caaaaccaag ggcggtcacc    6780
gttaccgcat caaggaacta ctgccaaagg acgtacgcc gccctctcat cgaatgtacg    6840
cgatgatggc cttgcgagcg gatggatcga aggtctatct gccggtgcgg aatgaggact    6900
tggccctcta cgaggaagcc caagaacgcc ttgctacaga ggcactgccg ctgccgaaaa    6960
cctctgttcg acctggccac aacaccgacc aggcgcgcgg ctacaactac acccaatggc    7020
gcgacttctt caatgcgcgc caactgctgt gccttggcct gctgctgcgg gaaatcctga    7080
ccatcgacga cctggcagtg caagagcaga tgctgtgctt gttctccagc accttggagt    7140
tcaacaacct gttttgcagc ttcaagggtg agggaacagg ggccgtgcgg catatgttct    7200
cgaaccacat cctcaagcca gagcgcaccc cgctggagaa ctccgtgtgg ggcactggca    7260
agagcagcgg tacgtttagc acgttgttcg agtctcgcct gctacgtgcg aagcgctacc    7320
tcgatgagcc gttcgagatc gcgttcgagc atgaccagga cggtaaccgc gcaggctcgc    7380
gcaagacggt ggctagccat ccgatccgcg cccgtcgcgt cgaaacctgg ccggaattgg    7440
aggccgcaga tcatggcctg ctgatcctca acggtgacag ctcgaagctg ccggtgcccg    7500
ctggttcggt ggatgccgtg gtgactgatc cgccctactt cgacttcgtt cattactcgg    7560
agttgagcga cttctttttt gcttggctca cccctgtgct gcgccagcgc tatccgtgga    7620
```

```
tggcccgcga ggactcgtct gaccaagggg aggtgcagca caaagaccct cgtgtgttcg      7680
cccgtcagct tgcgtcggtg ttcacggagg cgtgccgcgt gcttaaggac gatggagtgt      7740
tggcgttcag cttccaccac tcgcgtgccg agggctgggc ggccatctat gaagcgatca      7800
acaaggcggg cctggccgta gttgcggctc accctgtcca tgccgagctg cgcgcggcaa      7860
gtcccaagac tgcggccaaa gacccgatca gccttgatgc gattctggtg tgtcgcaaaa      7920
aggcgtttgc cctgcaccag tcgcctgcta tccaggatgt ccgccaggct gttgatgcgc      7980
tggcatcacg gctgcaagct gctggccttc gcatctcggc gggtgaccgc ttcgtgatcg      8040
gcgcagcgca aaccttgatt gcacgcgctg ctgatgacat gggcttcgac gagatcaagg      8100
ttgatcttga ggcaattcgg ctggccgtgg ggccaagggc tgcaacatca aaggctgcga      8160
gtgcgtggga tgacgatgtg cccttctgat tggctgcacg gccttgtcgg cgcatgcgtt      8220
ttgatggcag ccgctgcacg caagccgcgt ccctccgcgt aaagttcatt tatacgcaaa      8280
tacgtatttg cgtgatacaa taacgccata ttaatggagg tgcgtaaatg cggactattg      8340
ttgtggctag ccaaaaaggt ggcgtcggca agacaacgat tgcaggtcac ttgggtgtca      8400
tggccgagca gagcaaagag gggccagtgg cgctgatcga cacagaccca caaggctcgc      8460
tcgcgtcctg gtggaatgag cgaaccaatg aggcaccgct gtttgcacgg gtggaaatcg      8520
gcaagctgac cgagcacctt caggcattgt ccaagggtgg catcaagctg ccatcatcg       8580 acaccccgcc ctctgttacg gaaatgattc agcaggtgct ccgcaccgcc gacttggtac      8640
tgatccccac caggccgagt ccgcatgact tgcgcgcgt cggatctacc gtcgaactgg       8700
tggagaacgc aggcaagcga atgatcttcg tcatcaatgg ggcggcacct cgcgcgcgga      8760
tcgcgggtga ggctgccgtg gcgctttcgc agcatggcac ggttgccccc gtgacgctgt      8820
accagcgcac cgacttcgcc agctcgatga tcgacggccg caccgtccag gaaatcgacc      8880
ccaaggggcg gtcggccgaa gaaatcgggc agttgtggaa atacgtatct acacaactgc      8940 gtaaaattg atataatacg tacatgcgta ttaatggaga tacgtaaatg ctaaaactg        9000 catctttgac tgccggcctg gtggccaaga aaggggaggc gtcccctgct acggttgtcg      9060 cggcaccca ggttcaacct atcgaagtga aggcatcggc gactggcggc ggcccgggatt      9120 actacaaggc gttgaccgtc aagttggatc gtgaccgcta cgagagtctg aaaagcatgg      9180
gcgtgaagct ggacaagaag agccaggaaa tctttgtcga ggccctggat ttgtggatga      9240
agtcggccgc tggccagcaa cacgcctaag aggcccctat gcgttcagtg cgctctgccg      9300
tcgaactcgc caaggagttg gccgaaaaag ccaaggcccg ccgcctagcg gcggaaaaga      9360
acgagctggg acttgaaggc ccggcgcagg gcaacgccgg caccactccc agcccggtga      9420
aggttgcggc cgaagtggtg ggcgagcagc cggcacgacg caaggagcg ccgaaagggc       9480 cgcgtggcct gatgccggtg catcatccaa accgcgattt cttcttgtgc gatctgtttg      9540 actacgcccct aaaggatgac ggcgtgagca tggaggcccc catcttcacc ttggcaacca     9600
ggccggacac ctctgtttgg cattgggaaa gcaaggatgg gacacgcgcc atcaccgtca      9660
cgccaagcgt gaaggggagg gccacgcagt ttgataagga tttacttatt tacgtagtta     9720
gccagatgac cgaggctatc aatcgcggtc ggcctgatga gaacaatcga accgtgcgct      9780
ttcgcgtcta tgactacttg gtctcaacca acaagccgac tggcggcaag gagtaccagc      9840
gactggagga tgccctagac aggctgcggg gtacatcgat caagacgaac atcaagacgg      9900
gtggccagcg tgtgaaggaa ggcttcggca tcgtcgtatag ctggacgatc atcgagaagg    9960
```

```
cccccgacga tgaccgcatg attgccgtcg aggtcacgct ctccaagtgg cttttcaatg    10020
cagtgcaggc ccacgaggtt ctgaccatca acccggacta tttccggctg cgtaagccaa    10080
ttgagcgccg tttgtacgag ctggccagga agcactgtgg cgaccaggcc ttttttgtga    10140
ttgggctgga actgttgcag gacaagtgcg gcagcaagtc ggcactgttc gagttccgcc    10200
gtgccttgcg cgagatcatc aaggccgaca ccttgccaga ctaccgcatg acgcttgatg    10260
acgagaaaga ccaggtgatt ttctacaccc gcgacacgaa gaagctagcg gcgtctaccg    10320
ctctggcccg gcgcttccag tgacgcccaa agtattgacg gtcaatactt cgttatttca    10380
cccatgcggt gttaccgctg cgtgttggac gttcccttga cctagcggcc gaggcagggc    10440
tttcgcgctt tgcattgagc caccaagtgc gtctcgctcc ttcgagcatc aagccctaac    10500
gcgtttcatg tcactttcgc gcacgaaagt cgaggcaaga ggcttgatcg tgtctatcgt    10560
tacatcaccc atgcctgtgg atggacacgt tacatcaccc atgttttctg tggatgggca    10620
cgttacatca cccatacctc acttcgttac atcgccatg cagcgatttg tggaagcctt    10680
gagcagcaag gctttacgag cgttatccac agccgtaaca cgcgcgcgcg attttttaac    10740
tttataaatc tttaacgcgg ttgcggacaa agcccgcgcc gcctcttggg ggctacgccc    10800
ccgccggctc ctacgggccg caagcggccc tccgcccgcg cttcgcgctc cctcccggca    10860
tccccgaggg gtttcgcttc gctgcacccc tcgcgcttcg cgctcacccg catatcgagg    10920
cccccaaagg gggccggatg gtgccccc                                      10948
```

<210> SEQ ID NO 3
<211> LENGTH: 23
<212> TYPE: DNA
<213> ORGANISM: Artificial Sequence
<220> FEATURE:
<223> OTHER INFORMATION: Primer H-DEFB103A-U

<400> SEQUENCE: 3
tggggtgaag cctagcagct atg                                             23

<210> SEQ ID NO 4
<211> LENGTH: 24
<212> TYPE: DNA
<213> ORGANISM: Artificial Sequence
<220> FEATURE:
<223> OTHER INFORMATION: Primer H-DEFB103A-L

<400> SEQUENCE: 4
atgattcctc catgacctgg aaca                                            24

<210> SEQ ID NO 5
<211> LENGTH: 24
<212> TYPE: DNA
<213> ORGANISM: Artificial Sequence
<220> FEATURE:
<223> OTHER INFORMATION: Primer H-DEFB4-U

<400> SEQUENCE: 5
ccatcagcca tgagggtctt gtat                                            24

<210> SEQ ID NO 6
<211> LENGTH: 24
<212> TYPE: DNA
<213> ORGANISM: Artificial Sequence
<220> FEATURE:
<223> OTHER INFORMATION: Primer H-DEFB4-L

<400> SEQUENCE: 6

```
cgcctatacc accaaaaaca cctg                                          24

<210> SEQ ID NO 7
<211> LENGTH: 24
<212> TYPE: DNA
<213> ORGANISM: Artificial Sequence
<220> FEATURE:
<223> OTHER INFORMATION: Primer H-S100A7-19U

<400> SEQUENCE: 7
cactcatcct tctactcgtg acgc                                          24

<210> SEQ ID NO 8
<211> LENGTH: 24
<212> TYPE: DNA
<213> ORGANISM: Artificial Sequence
<220> FEATURE:
<223> OTHER INFORMATION: Primer H-S100A7-142L

<400> SEQUENCE: 8
ggcttggctt ctcaatcttg tcat                                          24

<210> SEQ ID NO 9
<211> LENGTH: 23
<212> TYPE: DNA
<213> ORGANISM: Artificial Sequence
<220> FEATURE:
<223> OTHER INFORMATION: Primer H-RNASE7-U

<400> SEQUENCE: 9
gagtcacagc acgaagacca agc                                           23

<210> SEQ ID NO 10
<211> LENGTH: 20
<212> TYPE: DNA
<213> ORGANISM: Artificial Sequence
<220> FEATURE:
<223> OTHER INFORMATION: Primer H-RNASE7-L

<400> SEQUENCE: 10
agcagcagaa ggggggcagaa                                              20
```

BACTERIUM AND EXTRACTS OF SAID BACTERIUM AND THE USE OF SAME IN THERAPY

The subject matter of the claimed invention was developed under a joint research agreement. The parties to this joint research agreement include Université Pierre et Marie Curie (Paris 6), Centre National De La Recherche Scientifique (CNRS), Pierre Fabre Dermo-Cosmétique and Pierre Fabre Médicament. The joint research agreement was in effect on or before the date the claimed invention was made and the claimed invention was made as a result of activities undertaken within the scope of the joint research agreement.

The present invention relates to a novel bacterial strain isolated and characterized from groundwater. The invention also relates to bacterial extracts and to the therapeutic use of same, notably in the context of the treatment of inflammations.

More particularly, the present invention relates to novel compositions of interest in the treatment and the prevention of chronic intestinal inflammatory disorders and periodontitis.

Acute colitis, irritable bowel syndrome and Crohn's disease are diseases that are increasing in developed countries and affect approximately 1.4 million Americans. (Arijs, I. et al., 2009. PLoS ONE.4:e7984, and Hill, D. A. and D. Artis. 2010. Annu. Rev. Immunol. 28:623-67 and Kaser, A. et al., 2010. Annu. Rev. Immunol. 28:573-621). Crohn's disease, an inflammatory intestinal disease, affects segments of the digestive tract, but its preferential sites are the ileum (terminal portion of the small intestine) and the colon. The wall of the affected intestine is edematous. During its progression, this edema of the intestinal wall will cause a decrease in the diameter of the intestine. Evolution toward fibrosis, a source of stenosis (contraction), may also occur.

The disease is characterized by the presence of ulcerations, more or less wide and more or less deep, which pass through the wall (fissures) thus causing abscess and fistulas. This disease affects both sexes and appears in general between the ages of 20 and 40. In its typical form, it begins slowly and insidiously. Episodic diarrhea and indistinct abdominal pain summarize the symptomatology for months or years.

When the disease has firmly taken hold, diarrhea of moderate intensity, sometimes fatty and seldom bloody, is the principal symptom. Fixed and continuous pain in the right iliac fossa or paroxysmal or atypical pain is also associated with the disease. Weight loss and fever are other important symptoms. The signs vary according to the topography of the lesions.

The disease progresses by flare-ups that are variable in intensity and that often regress spontaneously.

Complications are, however, frequent and they may require multiple surgical procedures: intestinal obstruction, intestinal fistulas, intestinal perforations, fistulas (openings) in the skin or in intra-abdominal organs, anorectal complications (fissures, abscesses).

Aside from surgical procedures, treatments with monoclonal antibodies (anti-TNF, anti-IL-12/p40 or anti-IL-23/p40) exist to palliate Crohn's disease but they have the disadvantage of being very costly.

The invention of the present patent application, in this context, proposes a different, effective and much less costly approach for relieving patients suffering from this disease.

Crohn's disease is multifactorial and complex. One of the factors identified in this disease is immunological in nature.

Recent publications have revealed that the immune system of the host is "disrupted": pro-inflammatory and inflammatory reactions have proven to be disproportionate and exacerbated. A deregulation of the immune system is suggested: Th1 profile potentiated with production of IL-12, Th17 profile potentiated with an increase in IL-23, disruption of the natural flora of the intestine and impaired tolerance, which leads to inappropriate local and systemic immune responses resulting in immune responses against the aberrant intestinal flora leading to pathogenesis (activation of T cells, inflammatory cytokines, antibodies against intestinal bacteria) (Abraham C. and Cho J. H., N Engl J Med 2009; 361:2066-78).

Cenac et al., (Am J Pathol. 2002. 161:1903-1915) discovered that the activation of proteinase-activated receptor-2 (PAR2) induced acute intestinal inflammation in animals. PAR2 is overexpressed in the gastrointestinal tract: endothelial cells, colonic myocytes, enterocytes, enteric neurons, immune cells, etc. Proteases (trypsin, tryptase) present in abundance in the gastrointestinal tract cleave the PAR2 at the N-terminal exposing a specific peptide which activates this same receptor (phenomenon of self-activation). Consequently, this activates the production of pro-inflammatory cytokines and triggers inflammation (Vergnolle, N. 2005. Gut. 54:867-874 and Vergnolle, N. 2009. Pharmacol. Ther. 123:292-309). This phenomenon is observed in the wild mouse but does not appear in the KO mouse (PAR2 deficient). Treatment with an antiprotease and/or a PAR2 antagonist makes it possible to avoid this inflammation phenomenon.

Similar to gingivitis, periodontitis is an inflammatory disease of the periodontium, i.e., specialized tissues that surround and support the teeth: the gum, the cementum, the periodontal ligament and the alveolar bone. It is often accompanied by alveoloclasia (bone loss). Chronic periodontitis may appear at any age but is more common in adults. It is multifactorial (genetic and environmental factors). Chronic periodontitis is initiated and maintained by dental bacterial biofilm.

However, immune defense mechanisms play an important role in its pathogenesis. Recent studies revealed that PAR2 plays an important role in periodontitis because it is expressed in osteoblasts, in oral epithelial cells and in gingival fibroblasts (Holzhausen, M. et al., 2006. Am J Pathol. 168:1189-1199).

It has been reported that gingipain-R proteases produced by *Porphyromonas gingivalis* (major pathogen in chronic periodontitis) are able to activate PAR2 by proteolytic cleavage of the N-terminal thus exposing a specific peptide which activates this same receptor (phenomenon of self-activation) (Abraham, L. A. et al., 2000. Bone. 26:7-14 and Lourbakos, A. et al., 2001. Infect. Immun. 69:5121-5130). This induces the production of pro-inflammatory cytokines followed by inflammation which results in bone loss.

Therapy targeting protease inhibition or the use of a PAR2 antagonist constitutes a possible approach for modulating pathologies of infectious origin such as an inflammatory disease like periodontitis.

In this context, the present invention provides a solution to the treatment of these inflammatory disorders by the isolation, the characterization and the fractionation of a novel bacterium never before described.

For the first time, and in a surprising manner, the Applicant succeeded in isolating a strain belonging to a novel bacterial species from groundwater, wherein said novel bacterial strain (or bacterium) is named LMB64.

This bacterium LMB64, in addition to the fact of having been isolated, was characterized and defined as belonging to the class of Betaproteobacteria, subfamily of Neisseriaceae, and probably of a novel genus not yet defined. Analysis of the gene sequence coding for 16S rRNA made it possible to place this bacterium close to the genera *Chromobacterium, Paludimonas, Lutelia* and *Glubenkiana*, with which it shares 95% sequence similarity.

This nonpathogenic bacterium is Gram-negative and will be described in greater detail in the examples. This bacterium also has the characteristic of being nonfilamentous. Moreover, this bacterium has the advantage of being able to be cultured on a medium containing any type of water, and more particularly, ordinary water. As an example, in contrast to *Vitreoscilla filiformis* (*V. filiformis*), the culture of bacterium LMB64 of the present invention does not require particular culture conditions and, more particularly, does not require a medium containing at least one sulfur-free type of mineral and/or thermal water (mention may be made in this respect to the patent document EP2018891 (Guéniche A., 2009) and the document by Guéniche et al. 2006 (European Journal of Dermatology, 16, 4, 380-384) which describe the use of a bacterial extract of *V. filiformis* for the treatment of atopic dermatitis). This represents a clear advantage in terms of both culture conditions and facilities and from an economic point of view.

The gene coding for 16S rRNA has been almost completely sequenced (1487 bp). Bacterium LMB64 has a circular plasmid of 10948 bp. This plasmid was completely sequenced and the sequence is represented in sequence SEQ ID No. 2.

According to a first embodiment, the present invention relates to a nonpathogenic Gram-negative bacterium belonging to the class of Betaproteobacteria, subfamily of Neisseriaceae, whose nucleotide sequence of the gene coding for 16S rRNA includes or comprises the sequence SEQ ID No. 1, or any nucleotide sequence with at least 80%, preferably 85%, 90%, 95% and 98% identity with said sequence SEQ ID No. 1.

In a preferred manner, the present invention relates to a nonpathogenic Gram-negative bacterium belonging to the class of Betaproteobacteria, subfamily of Neisseriaceae, characterized in that the nucleotide sequence of the 16S rRNA gene of said bacterium includes or comprises the sequence SEQ ID No. 1.

In the context of the present invention, "percentage identity" between two nucleic acid sequences refers to a percentage of identical nucleotides between the two sequences to be compared, obtained after the best alignment (optimal alignment), wherein this percentage is purely statistical and the differences between the two sequences are distributed randomly and over their entire length. Comparisons of sequences between two nucleic acid sequences are normally made by comparing these sequences after having aligned them in an optimal manner, wherein said comparison may be made per segment or per "comparison window." The optimal alignment of the sequences for the comparison can be carried out, in addition to manually, by means of the local homology algorithm of Smith and Waterman (1981) [Ad. App. Math. 2:482], by means of the local homology algorithm of Needleman and Wunsch (1970) [J. Mol. Biol. 48:443], by means of the similarity search method of Pearson and Lipman (1988) [Proc. Natl. Acad. Sci. The USA 85:2444] or by means of computer software using these algorithms (GAP, BESTFIT, FASTA and TFASTA in the Wisconsin Genetics Software Package, Genetics Group Computer, 575 Science Dr., Madison, Wis., or the BLAST N or BLAST P comparison software).

The percentage identity between two nucleic acid sequences is determined by comparing these two aligned sequences in an optimal manner wherein the nucleic acid sequence to be compared may include additions or deletions in relation to the reference sequence for an optimal alignment between these two sequences. Percentage identity is calculated by determining the number of positions for which the nucleotide is identical between the two sequences, by dividing this number of identical positions by the total number of positions in the comparison window and by multiplying the result obtained by 100 to obtain the percentage identity between these two sequences.

For example, the "BLAST 2 sequences" program (Tatusova et al., "Blast 2 sequences—a new tool for comparing protein and nucleotide sequences," FEMS Microbial Lett. 174:247-250), may be used with the default parameters (in particular for the parameters "open gap penalty": 5, and "extension gap penalty": 2; with the selected matrix being for example the "BLOSUM 62" matrix proposed by the program), with the percentage identity between the two sequences to be compared being calculated directly by the program. It is also possible to use other programs such as the "ALIGN" or "Megalign" software (DNASTAR).

According to another embodiment, the bacterium according to the invention includes at least one plasmid comprising sequence SEQ ID No. 2, or any sequence with at least 80%, preferably 85%, 90%, 95% and 98% identity with said sequence SEQ ID No. 2.

In a preferred manner, bacterium LMB64 includes at least one plasmid comprising sequence SEQ ID No. 2.

According to a preferred embodiment of the invention, bacterium LMB64 is characterized in that it is nonfilamentous.

Other characteristics of said bacterium LMB64 will be detailed below in the examples.

Moreover, bacterium LMB64 of the present invention has been deposited in the name of the Applicant with the *Collection Nationale de Cultures de Microorganismes* (CNCM), Institut Pasteur, Paris, on Apr. 8, 2010, under the reference I-4290.

Thus, one object of the invention is the bacterium deposited with the CNCM on Apr. 8, 2010, under the reference I-4290, or a homologue, a descendant or any other mutant.

The term "mutant" refers to any bacterium directly arising from strain I-4290 and may comprise natural mutations or recombinations, such as, for example, any recombination related to cell proliferation, cell division (mutation due to errors occurring during bacterial division or DNA replication) or any other mechanism of natural selection or of selection in culture media, such as the selection of mutants that are resistant or that become resistant to a given compound. Included among these mutants are any bacteria arising from strain I-4290 comprising one or more mutations in their genomic sequence (or that of their plasmid), in which the mutations were caused by radiation, by a virus, by transposons or by mutagenic chemicals.

According to a first embodiment of the invention, from a bacterial culture, the entire biomass may be isolated by various known methods such as, for example, by filtration, coagulation with an alcohol (ethanol, isopropanol, isobutanol), by drying on a cylinder with a scraped prelayer, etc., and then used in freeze-dried or heat-inactivated form.

According to another preferred embodiment, the invention relates in a general manner to a bacterial extract, also called a bacterial fraction, obtained from a suspension of bacteria as described above, namely bacterium LMB64.

The term "bacterial extract" refers to any extract or fraction of the bacterial biomass or any active fraction of said extract. For example, such an extract may be obtained from a culture of bacterium LMB64 wherein the preparation method comprises at least one step of lysis of the bacteria and one step of separation of the various fractions of which it is constituted by centrifugation or by filtration.

In a nonrestrictive manner, the extract according to the invention may consist of bacterial cells isolated from the culture medium which have been concentrated, for example by centrifugation; or concentrated bacterial cells which have undergone an operation in which the cell envelope has been ruptured by any means known to those persons skilled in the art, such as by the action of ultrasound or autoclaving; or the supernatant obtained by filtration.

An important step of the extract preparation method according to the invention consists of the elimination of the various intracellular components such as, for example, nucleic acids (chromosomal DNA, extrachromosomal circular DNA, plasmids), ribosomes and intracellular stored substances such as glycogen, starch and poly-$\beta$-hydroxybutyrate, etc.

In a preferred manner, the bacterial extract according to the invention is obtained after treatment of said bacterial suspension in such a way as to eliminate the intracellular components.

The result is that the extract according to the invention primarily includes components arising from the membrane, from the periplasmic space and/or from the extracellular space.

More particularly, said intracellular components comprise at least the nucleic acids.

In addition to the elimination of intracellular compounds, and as a nonrestrictive example, it is also easily possible for those persons skilled in the art to separate, after lysis of the bacteria and centrifugation, the components of the culture supernatant (hereafter fraction S0) and the components constituting the pellet (hereafter E0). For example, it may be suggested that the separation threshold between the constituents of S0 and E0 is around a molecular weight of 100 kDa. Consequently, the constituents of fraction S0 have, for the most part, a molecular weight less than 100 kDa, whereas the components of fraction E0 have, for the most part, a molecular weight greater than 100 kDa.

More particularly, it is thus possible by techniques known to those persons skilled in the art to extract and separate the biomolecules found in the culture supernatant (S0) from those mainly comprised of surface proteins and proteins located in the periplasmic space of the bacterium (E0).

According to one embodiment of the invention, the bacterial extract includes a fraction E0 comprising at least membrane proteins, periplasmic proteins and proteins arising from the flagellum.

Periplasmic proteins include proteins lodged in the periplasmic space of Gram-negative bacteria which may be released by osmotic shock or by incubation in a medium containing a chaotropic agent or detergents (Molecular Cloning: A Laboratory Manual, 3$^{rd}$ edition: Sambrook and Russell. CSHL Press).

Proteins arising from the flagellum include multimeric proteins of the flagellum or fragments of the flagellum. Methods for isolating and purifying whole bacterial flagella with detergents followed by ultracentrifugation separations (in the presence of a CsCl gradient) are described in the literature. In the invention, the examples of extraction methods made it possible to recover flagella fragments.

Membrane proteins include proteins that are anchored in the membrane and of which a part is exposed on the surface (such as outer membrane proteins, or Omp), proteins that are adhered to the surface of the membrane, lipoproteins and porins (Ward J B., Microbial adhesion to surfaces, 1980).

In a preferred manner, said membrane proteins consist of porins, OmpA, lipopolysaccharides and/or lipoproteins.

According to another embodiment of the invention, it may be preferred to use fraction S0.

More particularly, the bacterial extract according to the invention includes a fraction S0 comprising at least secreted peptides and proteins and secondary metabolites.

Secreted peptides and proteins include peptides and proteins that are naturally produced and secreted by bacterium LMB64 and which may be recovered by centrifugation or by filtration.

Secondary metabolites include the small molecules that bacterium LMB64 produces and secretes in the culture medium.

The presence of lipopolysaccharides within fraction S0 should be mentioned here. Indeed, lipopolysaccharides, although they are found primarily in fraction E0, are nevertheless also found in smaller quantities in fraction S0.

In an advantageous manner, fractions E0 and S0 may be combined in such a way as to obtain a fraction ES0 by leaving, for example, the culture medium to incubate and to react in basic medium (pH 9 to 11) for approximately 5 hours a temperature of 4° C., by centrifuging and by filtering at 0.2 µm in order to obtain a clear ES0 solution.

Bacterial extract ES0 is thus composed, among other things, of membrane proteins, lipopolysaccharides, periplasmic proteins, protein fragments of the flagellum and primary and secondary metabolites produced by the bacterium.

In a preferred way, extract ES0 has a protein profile comprising at least, according to the SDS-PAGE technique, twelve bands including three principal bands corresponding, respectively, to molecular weights (approximately in relation to molecular standards from Bio-Rad) ranging between:
  band 1: 30 kDa and 36 kDa, preferentially 34 kDa;
  band 2: 41 kDa and 45 kDa, preferentially 43 kDa;
  band 3: 47 kDa and 51 kDa, preferentially 49 kDa.

According to another embodiment of the invention, the bacterial extract includes a fraction ES0 comprising at least fraction E0 and fraction S0.

According to a preferred embodiment of the invention, the bacterial extract includes a fraction ES0 with a protein profile, obtained by SDS-PAGE, which includes three principal bands corresponding to molecular weights ranging between 30 kDa and 36 kDa, 41 kDa and 45 kDa, and 47 kDa and 51 kDa, respectively.

According to a preferred embodiment of the invention, the bacterial extract includes a fraction ES0 with a protein profile, obtained by SDS-PAGE, which includes three principal bands corresponding to molecular weights of 34 kDa, 43 kDa and 49 kDa, respectively.

According to another aspect, the invention describes a method for preparing a bacterial extract comprising the steps of:
  a) culturing bacterium LMB64 in a suitable medium; and
  b) eliminating the intracellular components.

According to another embodiment, the method according to the invention consists of a method for preparing a bacterial extract S0, wherein said method comprises the steps of:

a) culturing bacterium LMB64 in a suitable medium;
b) centrifuging said culture; and
c) recovering supernatant S0.

According to another embodiment, the method according to the invention consists of a method for preparing a bacterial extract E0, wherein said method comprises the steps of:
a) culturing bacterium LMB64 in a suitable medium;
b) centrifuging said culture and eliminating the supernatant;
c) treating the biomass resulting from step b) in such a way as to eliminate the intracellular components; and
d) recovering the pellet E0.

In a preferred manner, step c) consists of ultrasonic treatment of the biomass resulting from step b) and then an initial centrifugation aimed at eliminating the pellet comprising said intracellular components and then a second centrifugation of the supernatant.

According to another embodiment, the method according to the invention consists of a method for preparing a bacterial extract E0, wherein said method comprises the steps of:
a) culturing bacterium LMB64 in a suitable medium;
b) centrifuging said culture and eliminating the supernatant;
c) treating with ultrasound the biomass resulting from step b);
d) centrifuging said biomass treated with ultrasound and eliminating the biomass obtained;
e) centrifuging the supernatant resulting from step d); and
f) recovering the pellet E0.

It should be noted that the various methods described above are provided for illustration only and that any methods known to those persons skilled in the art may be used.

As will become apparent from the examples below, the Applicant has demonstrated, in addition to the activities expected for this type of extract, several novel activities never before described.

A first advantageous aspect of the invention, related to immunomodulation, rests on the modulation property of pro-inflammatory cytokines. More particularly, the use of a bacterium and/or an extract according to the invention is able, in the case of a response strongly oriented toward a Th1 or Th17 profile as with Crohn's disease, to restore homeostasis.

Another advantage of the invention rests on the fact that, as will be apparent from the examples, the use of a bacterium and/or an extract according to the invention induces the production of antimicrobial peptides such as, for example but without being restrictive, peptides hBD-2, hBD-3, S1007A and LL-31. These peptides have an antimicrobial effect on pathogens that colonize the intestinal tract without affecting the normal growth of commensal microflora. As a result, their action restores normal microflora in the intestine.

More particularly, as mentioned above, an extract of bacterium *Vitreoscilla filiformis* (Guéniche A. et al., 2006) has been known with activity on TLR2, due to the presence of OmpA, and on TLR4, due to the presence of lipopolysaccharides. Because of the absence of flagella in the *V. filiformis* bacterium, the extract obtained from *V. filiformis* has no TLR5 activity.

For the first time, the Applicant describes a bacterial extract according to the invention which has, in addition to activity on TLR2 and TLR4, activity on TLR5.

The invention thus relates to the use of a bacterium and/or a bacterial extract such as described above as an activator of TLR2, TLR4 and TLR5.

In a preferred manner, said bacterial extract activator of TLR2, TLR4 and TLR5 consists of an extract comprising all or part of the proteins arising from the flagellum. In this case, as an example, said extract is preferentially extract E0 or extract ES0.

Said TLR5 activation activity is of significant interest in that TLR5 are known to induce certain antimicrobial peptides such as psoriasin (S100A7) and hBD-2 (Glaser et al., Journal of Investigative Dermatology (2009) 129, 641-649). Moreover, TLR5 agonists act in synergy with those of TLR2 and TLR4, thus making it possible to potentiate the production of antimicrobial peptides. It has been shown that by blocking TLR5 with an antibody, the latter are produced little or not at all.

This aspect is thus particularly innovative in terms of immunomodulation applications for the bacterium and/or the extracts according to the invention.

Thus, the invention also has as an object a method for the treatment or prevention of pathology, in particular pathology related to an infection or to an immune response defect, wherein said pathology is associated with a defect in the activity of TLR2, TLR4 and TLR5, and wherein said treatment or prevention involves modulation of the activity, in particular an increase in the activity, of said TLR2, TLR4 and TLR5 by the administration of an activator of said receptors, wherein said method comprises the administration, to a patient who has or who is likely to have said pathology, of an effective quantity of a bacterium or a bacterial extract according to the present invention.

Furthermore, in an unexpected manner, the Applicant has also demonstrated, in contrast to the bacterial extracts described to date, antagonistic activity toward PAR2. This activity is of significant interest in the context of anti-inflammatory treatments.

The invention thus relates, quite particularly, to the use of a bacterium and/or a bacterial extract such as described above as a PAR2 antagonist.

The invention also has as an object a method for the treatment or prevention of pathology, in particular pathology related to inflammation, wherein said pathology is associated with a dysfunction of PAR2, and wherein said treatment or prevention involves modulation of the activity of said PAR2 particularly by the administration of an antagonist of said receptor, wherein said method comprises the administration, to a patient who has or who is likely to have said pathology, of an effective quantity of a bacterium or a bacterial extract according to the present invention.

In a preferred manner, said PAR2 antagonist bacterial extract consists of extract S0 or extract ES0.

PAR2 is overexpressed in endothelial cells, colonic myocytes, enterocytes, enteric neurons, immune cells and keratinocytes. Proteases (trypsin, tryptase) present in abundance in the environment cleave the PAR2 at the N-terminal exposing a specific peptide which activates this same receptor (phenomenon of auto-activation). Consequently, this activates the production of pro-inflammatory cytokines and triggers inflammation (Vergnolle, N. 2009, Pharmacol. Ther. 123:292-309). This phenomenon is observed in the wild mouse but does not appear in the KO mouse (PAR2 deficient). Treatment with an antiprotease and/or a PAR2 antagonist makes it possible to avoid this inflammation phenomenon.

The combination and the synergy of all these activities give this bacterium LMB64, or any extract arising from this same bacterium, a high potential to treat inflammatory diseases and, quite particularly, inflammatory diseases in which PAR2 is involved and/or in which the immune system is weakened, disturbed or unbalanced.

The invention thus relates to the use of a bacterium such as described above and/or a bacterial extract arising from said bacterium for the preparation of a composition intended for the treatment and/or the prevention of gastrointestinal and oral inflammatory disorders.

In a preferred manner, said gastrointestinal and oral inflammatory disorders consist of Crohn's disease, colitis or periodontitis.

According to another embodiment, the invention of the present patent application relates to a composition comprising, as an active ingredient, at least one bacterium and/or one bacterial extract according to the invention.

The composition according to the invention relates to the treatment of gastrointestinal and oral inflammatory disorders.

In a preferred manner, said gastrointestinal and oral inflammatory disorders consist of Crohn's disease, colitis or periodontitis.

The invention thus relates to a pharmaceutical composition further comprising a pharmaceutically acceptable carrier.

In the present description, "pharmaceutically acceptable carrier" refers to a compound or a combination of compounds made part of a pharmaceutical composition that do not cause secondary reactions and that, for example, facilitate the administration of the active compounds, increase their lifespan and/or effectiveness in the body, increase their solubility in solution or improve their preservation. Said pharmaceutically acceptable carriers are well known and will be adapted by those persons skilled in the art according to the nature and the mode of administration of the active compounds selected.

Preferably, said compounds may be administered systemically by intramuscular, intradermal, intraperitoneal or subcutaneous route, or by oral route. The composition comprising the antibodies according to the invention may be administered in several doses, spread out over time.

Their optimal modes of administration, dosing schedules and galenic forms may be determined according to criteria generally considered in the establishment of a treatment adapted to a patient such as, for example, the age or the weight of the patient, the seriousness of the patient's general health, tolerance to the treatment and side effects noted.

The invention will be better understood upon consideration of the examples below which illustrate the invention without limiting its scope.

EXAMPLE 1

Selection and Characterization of Bacterium LMB64

Bacterium LMB64 was isolated from groundwater.

Figure 1:
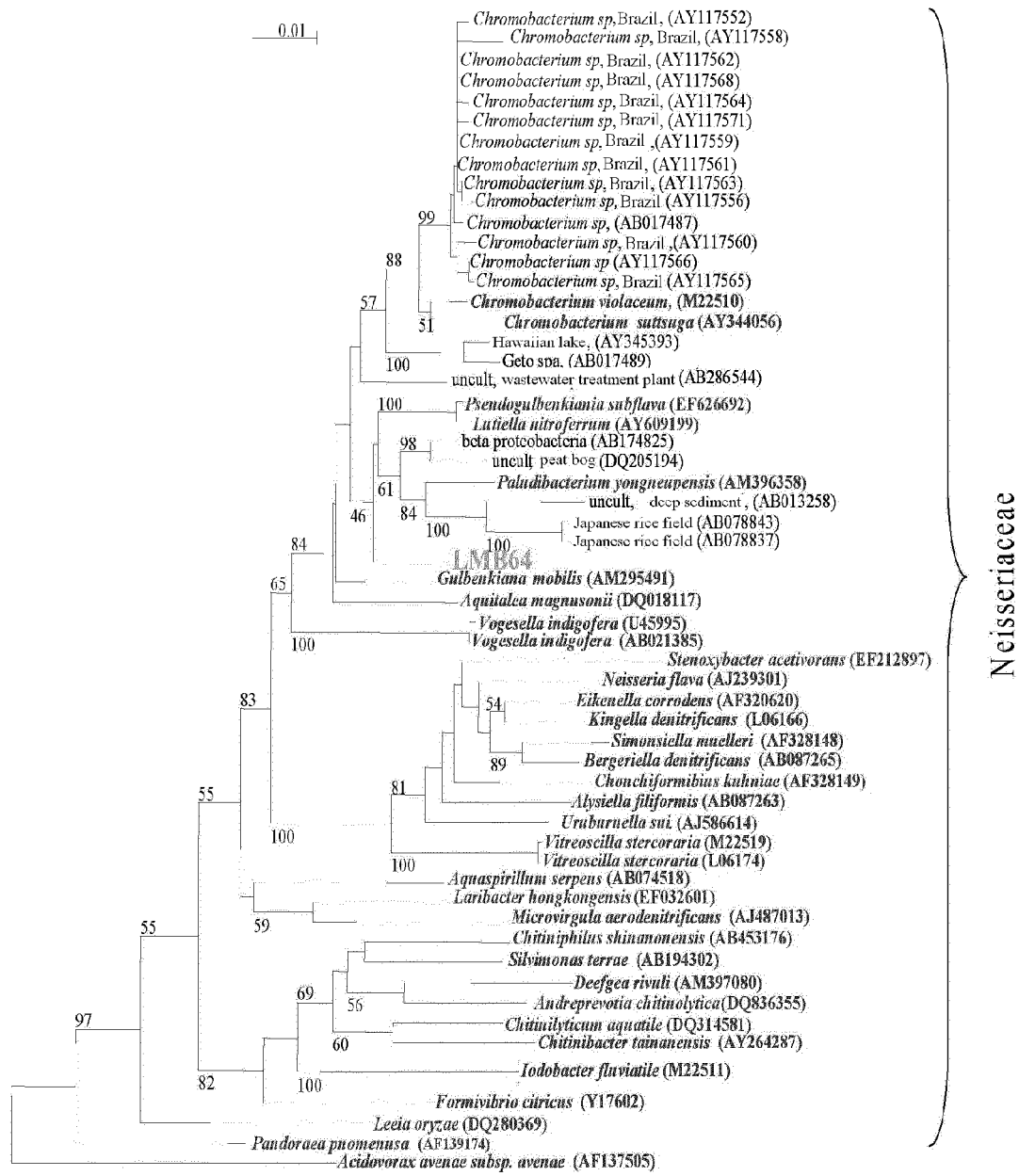
FIG. 1 illustrates the phylogenetic position of the sequence coding for the 16S rRNA of strain LMB64. The sequences appearing on this tree are sequences from the GenBank database closest to the sequence of LMB64.

The taxonomic position of novel bacterium LMB64 is proposed in FIG. 1.

Figure 2A:
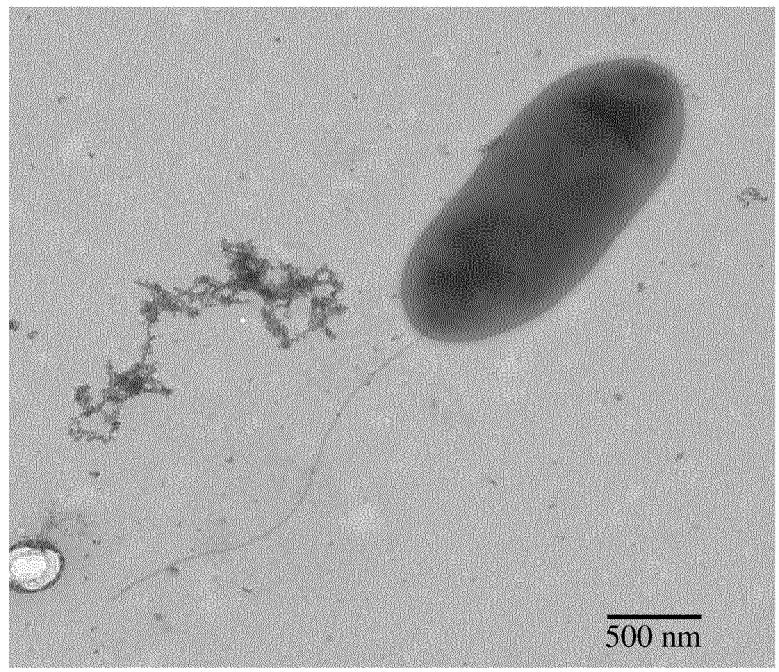
FIGS. 2A and 2B present images of bacterium LMB64 under the transmission electron microscope (A) and the scanning electron microscope (B).
Figure 2B:
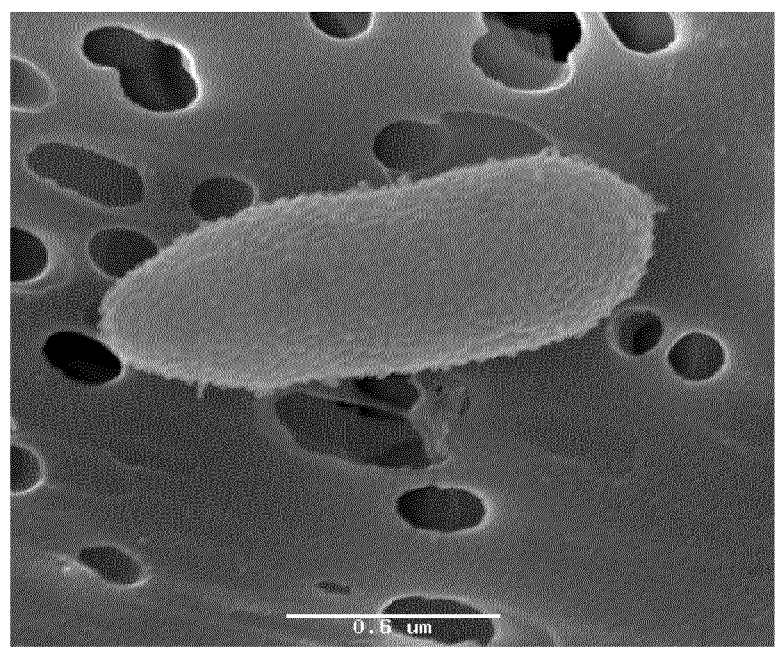

More particularly, bacterium LMB64 is rod-shaped with a length of roughly 2.3 μm (±0.3) and a width of roughly 1.0 μm (±0.1). A distinctive characteristic of this bacterium is the presence of a polar flagellum (FIGS. 2A and 2B). As can also be seen in these images, bacterium LMB64 is a non-filamentous bacterium.

As mentioned above, bacterium LMB64 has a circular plasmid of roughly 11 kpb. This plasmid was completely sequenced (SEQ ID No. 2).

The gene coding for 16S rRNA was also sequenced (SEQ ID No. 1). The bacterium was cultured in a fermentor in a synthetic medium. The growth rate is higher when the medium has a low concentration of carbon substrates.

The culture media tested are R3, MS-glucose and LB media whose compositions are described below in tables 1a, 1b and 1c, respectively.

TABLE 1a

| COMPOSITION OF R3 MEDIUM | |
|---|---|
| Yeast extract | 1 g/l |
| Difco proteose peptone | 1 g/l |
| Casamino acids | 1 g/l |
| Glucose | 1 g/l |
| Soluble starch | 1 g/l |
| Sodium pyruvate | 0.5 g/l |
| $K_2HPO_4$ | 0.6 g/l |
| $MgSO_4, 7H_2O$ | 0.1 g/l |

TABLE 1b

| COMPOSITION OF MS-GLUCOSE MEDIUM | |
|---|---|
| Glucose | 6.0 g/l |
| Citric acid | 0.84 g/l |
| $MgSO_4, 7H_2O$ | 0.25 g/l |
| $NH_4Cl$ | 1.06 g/l |
| Anhydrous $K_2HPO_4$ | 8.75 g/l |
| Pyruvic acid sodium salt | 0.5 g/l |
| Zinc sulfate, $7H_2O$ | 4 mg/l |
| Cobalt chloride, $6H_2O$ | 3.5 mg/l |
| Sodium molybdate, $2H_2O$ | 3.5 mg/l |
| Manganese sulfate, $1H_2O$ | 5 mg/l |

TABLE 1b-continued

COMPOSITION OF MS-GLUCOSE MEDIUM

| | |
|---|---|
| Boric acid | 2 mg/l |
| Concentrated hydrochloric acid | 50 mg/l |
| Copper sulfate, 5H$_2$O | 4 mg/l |
| Iron chloride, 6H$_2$O | 27 mg/l |

TABLE 1c

COMPOSITION OF LB MEDIA

| | |
|---|---|
| Tryptone | 10 g/l |
| Yeast extract | 5 g/l |
| NaCl | 5 g/l |

The growth rates of bacterium LMB64 as a function of culture medium are presented in table 2 below.

TABLE 2

| | Growth rate (/h) |
|---|---|
| LB | 0.25 (±0.05) |
| LB (½ dilution) | 0.46 (±0.11) |
| LB (⅕ dilution) | 0.60 (±0.14) |
| LB (¹/₁₀ dilution) | 0.69 (±0.15) |
| MS-glucose | 0.13 (±0.04) |
| R3 | 0.62 (±0.14) |

Figure 3:
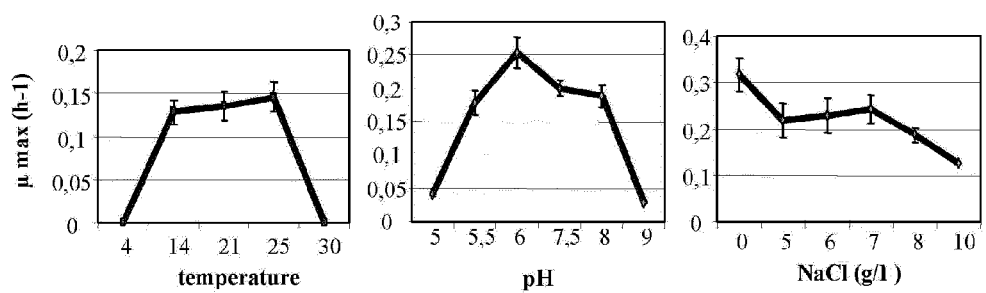
FIG. 3 presents growth optima determined as a function of the temperature, pH and salinity of the R3 culture medium.

The growth optima were determined as a function of the temperature, pH and salinity of the R3 culture medium (FIG. 3).

The sources of carbon assimilable by the bacterium were characterized using an API 50CH gallery (incubation temperature: 25° C.). The results are summarized in table 3 below.

TABLE 3

| | Incubation time | |
|---|---|---|
| | 4 days | 5 days |
| 1. Glycerol | | |
| 2. Erythritol | | |
| 3. D-arabinose | | |
| 4. L-arabinose | | |
| 5. D-ribose | | |
| 6. D-xylose | | |
| 7. L-xylose | | |
| 8. D-adonitol | | |
| 9. Methyl-β-D-xylopyranoside | | |
| 10. D-galactose | | |
| 11. D-glucose | + | + |
| 12. D-fructose | + | + |
| 13. D-mannose | | |
| 14. L-sorbose | | |
| 15. L-rhamnose | | |
| 16. Dulcitol | | |
| 17. Inositol | l | + |
| 18. D-mannitol | | |
| 19. D-sorbitol | | |
| 20. Methyl-α-D-mannopyranoside | | |
| 21. Methyl-α-D-glucopyranoside | | |
| 22. N-acetylglucosamine | | |
| 23. Amygdaline | | |
| 24. Arbutin | | |
| 25. Esculin/iron citrate | | |
| 26. Salicin | | |
| 27. D-cellobiose | | |
| 28. D-maltose | l | + |
| 29. D-lactose (bovine origin) | | |
| 30. D-melibiose | | |

TABLE 3-continued

| | Incubation time | |
|---|---|---|
| | 4 days | 5 days |
| 31. D-sucrose | + | + |
| 32. D-trehalose | l | + |
| 33. Inulin | | |
| 34. D-melezitose | | |
| 35. D-raffinose | | |
| 36. Starch | | |
| 37. Glycogen | | |
| 38. Xylitol | | |
| 39. Gentiobiose | | |
| 40. D-turanose | l | + |
| 41. D-lyxose | | |
| 42. D-tagatose | | |
| 43. D-fucose | | |
| 44. L-fucose | | |
| 45. D-arabitol | | |
| 46. L-arabitol | | |
| 47. Potassium gluconate | | |
| 48. Potassium 2-ketogluconate | | |
| 49. Potassium 5-ketogluconate | | |

+: usable substrate, l: low use

The enzymatic activities demonstrated on the API ZYM gallery are: alkaline phosphatase, esterase (C4), esterase/lipase (C8), leucine arylamidase, valine arylamidase, acid phosphatase, naphthol-AS-BI-phosphohydrolase, and α-glucosidase.

Bacterium LMB64 is sensitive to all the antibiotics tested as seen in table 4 below.

TABLE 4

| | Zone of inhibition diameter (mm) | | | Inhibitory |
|---|---|---|---|---|
| Antibiotics tested | R3 | LB ½ | LB ⅕ | activity |
| Ampicillin (10 µg) | 29 | 28 | 29 | + |
| Chloramphenicol (30 µg) | 29 | 26 | 24 | + |
| Ciprofloxacin (5 µg) | 38 | 34 | 34 | + |
| Kanamycin (30 µg) | 27 | 30 | 27 | + |
| Penicillin (6 µg) | 21 | 26 | 20 | + |
| Polymyxin B (50 µg) | 11 | 15 | 13 | + |
| Rifampicin (30 µg) | 20 | 19 | 15 | + |
| Tetracycline (30 µg) | 30 | 25 | 20 | + |
| Streptomycin (10 µg) | 25 | 25 | 24 | + |
| Vancomycin (30 µg) | 20 | 21 | 21 | + |

EXAMPLE 2

Method for Extracting Fractions E0, S0 and ES0

Preculture:

Strain AV13 is inoculated in an Erlenmyer flask containing 250 ml of MS glucose pyruvate medium (see table 5 below), followed by incubation under stirring for roughly 40 hours at 30° C. (pH 7) and 200 rpm until an OD$_{600}$≈1.5 is obtained.

TABLE 5

| MS Glucose Pyruvate | |
|---|---|
| Citric acid | 0.84 g |
| MgSO$_4$, 7H$_2$O | 0.25 g |
| NH$_4$Cl | 1.06 g |
| Anhydrous K$_2$HPO$_4$ | 8.75 g |
| Pyruvic acid sodium salt | 0.5 g |
| Oligo mix | 1 ml |
| ddH$_2$O qsp | 1000 ml |

TABLE 5-continued

| Verify pH | 7 |
|---|---|
| Autoclave | 121° C. 30 min |
| After autoclaving add: | |
| 20% glucose | 30 ml |

OLIGO MIX

Dissolve in 100 ml of distilled water:

| | |
|---|---|
| Zinc sulfate, 7H$_2$O | 4 g |
| Cobalt chloride, 6H$_2$O | 3.5 g |
| Sodium molybdate, 2H$_2$O | 3.5 g |
| Manganese sulfate, 1H$_2$O | 5 g |
| Boric acid | 2 g |
| Concentrated hydrochloric acid | 50 g |
| Copper sulfate, 5H$_2$O | 4 g |

Dissolve in 50 ml of distilled water:

| | |
|---|---|
| Iron chloride, 6H$_2$O | 27 g |
| ddH$_2$O qsp | 1000 ml |

Culture:

The preculture is then inoculated in a fermentor (Applikon) containing 3.7 l of MS pyruvate medium+114 ml of 20% glucose solution. A temperature sensor regulates the temperature preferably near 30° C. An oxygen sensor (AppliSens) is used to maintain the concentration of dissolved oxygen in the medium at 18-25%. A pH sensor (AppliSens) is used to maintain the pH at 7 by the addition of 10% NH$_4$OH via a fixed flow-rate pump. A Wedgewood Analytical sensor is used to monitor changes in optical density in real time. The culture is programmed in fed-batch mode; via a variable flow-rate pump the culture is supplied with 20% glucose solution. Fermentation is stopped when OD$_{600}$≈22-26, in general after roughly 30 hours.

Extraction S0:

The supernatant is separated from the biomass by centrifugation for 1 hour at 4° C. and 4000 g.

Extraction E0:

The wet biomass is taken up in NaCl solution (1 M). After centrifugation for 15 minutes at 4° C. and 9000 g, the supernatant is discarded and the pellet is taken up in 1 M NaCl solution. The sample tube is then plunged into a cooled ultrasonic bath at a power setting of 50-60 W for several minutes. After centrifugation for 30 minutes at 4° C. and 6000 g, the pellet is discarded and the supernatant is recovered. Two volumes of cold ethanol are added and the suspension is left overnight at 4° C. After centrifugation for 30 minutes at 4° C. and 6000 g, the supernatant is discarded and the pellet is taken up in 25 mM Tris buffer, pH 8.8.

Extraction ES0:

The culture is brought to basic pH (pH 9-11) with a base buffer. The next step is incubation under stirring for 5 hours at a temperature of 4° C. After centrifugation, the supernatant is prefiltered to eliminate remaining biomass debris and then filtered on a 0.2 μm filter. A clear yellow solution is obtained (ES0).

Proteins are assayed according to the DC Protein Assay Kit II (Bio-Rad) protocol. Sugars are assayed in glucose equivalent according to the phenol/sulfuric acid method (Dubois, M. et al., 1956).

As an example, table 6 below presents certain specific characteristics of extract ES0 as obtained under the conditions described above.

TABLE 6

| | Test batch | Preclinical batch 1 |
|---|---|---|
| Organoleptic characteristics | Homogeneous and translucent yellow-orange liquid Density near that of water | |
| pH (in the presence of base buffer) | 10.0 | 10.2 |
| Dry residue (thermobalance) | 5.9% | 5.1% |
| Protein profile (SDS-PAGE) | 12 detectable bands (including 3 principal bands roughly 34 kDa, 43 kDa and 49 kDa in size, respectively) | |
| Total protein assay (μBCA) | 2.9 mg/ml | 3.0 mg/ml |

It is clearly understood that the data above are presented here only for illustrative purposes.

More precisely, the data relate to a protein profile obtained by SDS-PAGE exhibiting three principal bands.

SDS-PAGE Protocol:

Extract ES0 is taken up in buffer (20 mM Tris-HCl, pH 8.0; 1 mM EDTA; 2.5% SDS and 0.01% bromophenol blue) and 1 M DTT (1,4-dithiothreitol). The sample and the mixture of molecular weight markers (WesternC, Bio-Rad) were deposited respectively in wells of an 8-16% SDS-PAGE acrylamide gel (GeBaGel, Gene Bio-Application). The migration buffer contains 2.5 mM Tris, 19.2 mM glycine and 0.01% SDS (w/v). Migration is allowed to proceed under a constant voltage of 160 V for approximately 1 hour (GeBaGel system). The protein bands were then stained with Coomassie Blue (Instant Blue, Expedeon). Sizes were calculated in relation to known standards (STD).

Figure 10:
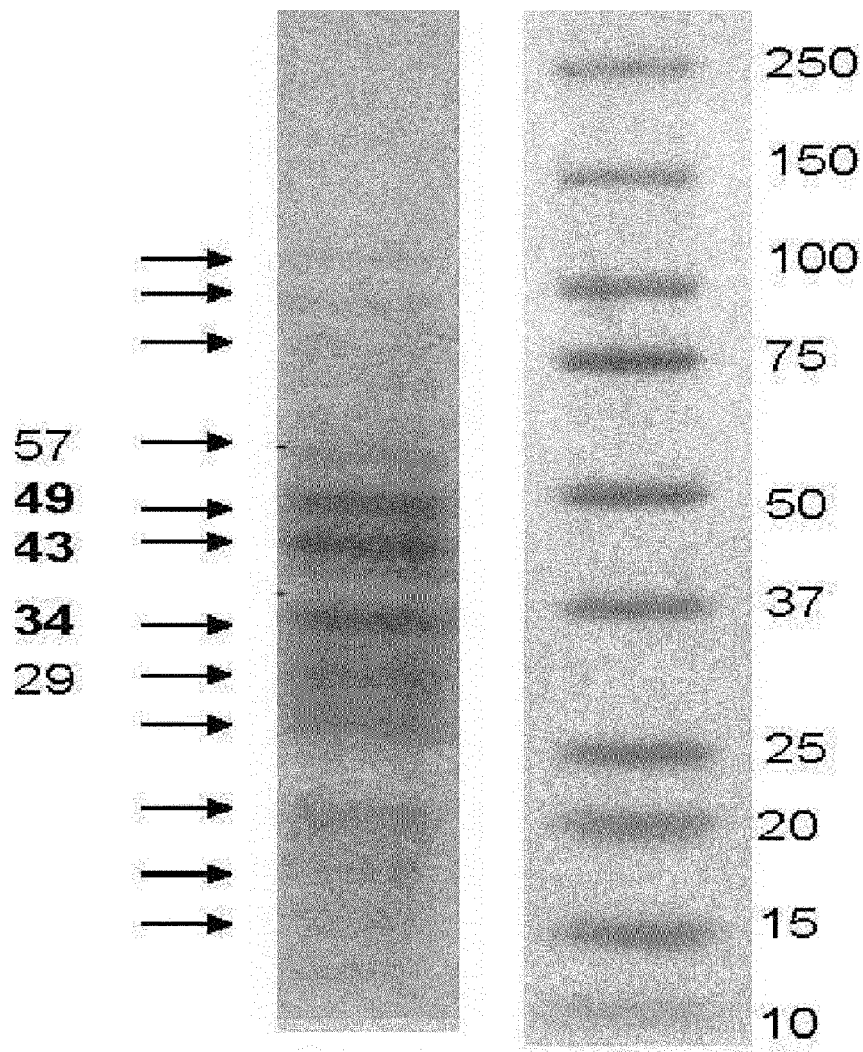
FIG. 10 consists of an SDS-PAGE gel of extract ES0.

The gel obtained is presented in FIG. 10.

According to one embodiment of the invention, these three bands have molecular weights of approximately 34 kDa, 43 kDa and 49 kDa, respectively.

EXAMPLE 3

Demonstration of the Pharmacological Activities of Fractions E0 and ES0

Langerhans cells (LC) are generated in vitro from human monocytes isolated from Buffy-Coat pouches from the French National Blood Service (*Etablissement Français du Sang* (EFS) *Pyrénées Méditerranée*): isolation on a Ficoll gradient (Lymphocyte Separation Medium, density 1.077 g/ml) and purification by magnetic immunoselection (Miltenyi Biotec); LC differentiation is carried out for 6 days in the presence of a cytokine cocktail (GM-CSF/IL-4/TGFβ). LC distributed on 24-well plates in RPMI-5% FCS culture medium are incubated for 24 hours with extract ES0.

Surface molecules are analyzed by flow cytometry (FACSCalibur, BD Biosciences) with triple or quadruple staining: CD1a/CD54/CD80/CD83/CD86/FcεRI; cytokines secreted in the culture supernatants are analyzed with the Cytometry Bead Array (cat. no. 550749, BD) in flow cytometry: IL-6, IL-8, TNF, IL-4, IL-10, IL-12.

3.1 Langerhans Cell Maturation and IgE Receptor (FcεRI) Inhibition

Figure 4:
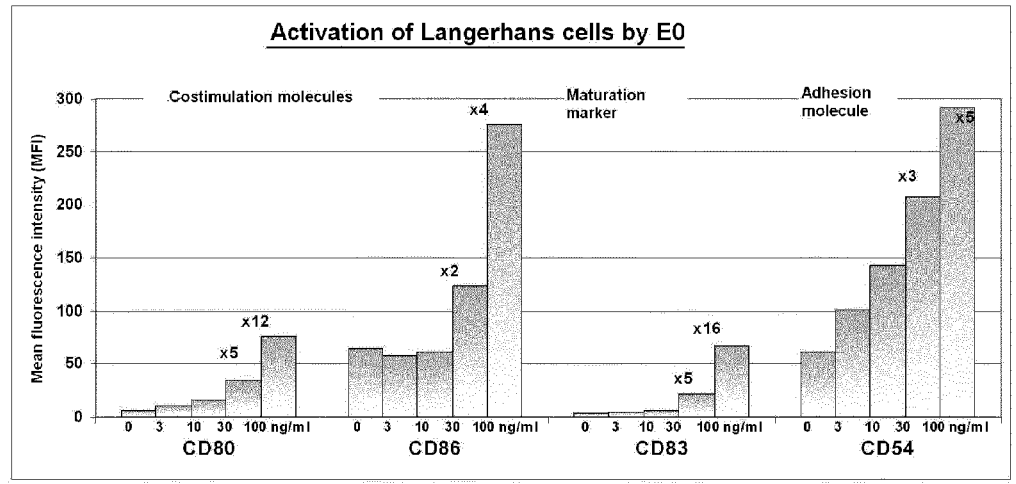
FIG. 4 illustrates induction of surface molecules CD80, CD86, CD83 and CD54 by extract E0 (dose-dependent effect).
Figure 5:
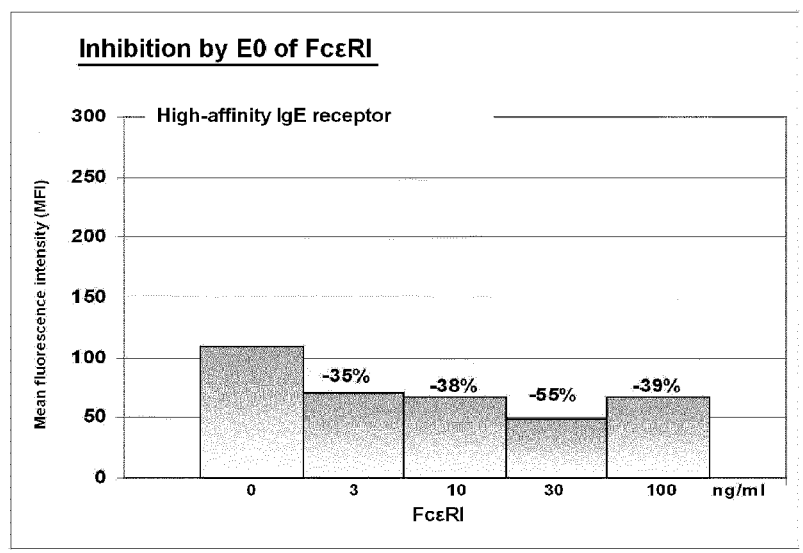
FIG. 5 illustrates inhibition of IgE receptors by extract E0.

Extract E0 induces the maturation of Langerhans cells observed by dose-dependent induction of surface molecules CD80, CD86, CD83 and CD54 (FIG. 4). Similarly, extract E0 inhibits the expression of IgE receptors (FcεRI) according to a dose-dependent effect (FIG. 5).

3.2 Activation of Toll-Like Receptors (TLRs)

The TLR activity of ES0 was evaluated on TLR2, TLR4 and TLR5 using the model of HEK293 cells cotransfected by the gene for TLR2, TLR4 or TLR5 and by the reporter gene NFκB-sAP (secreted alkaline phosphatase). The binding of a ligand to its TLR leads to the activation of the transcription factor NFκB; the sAP gene is placed under the control of a promoter that can be induced by NFκB. This reporter gene makes it possible to monitor cell signaling via TLRs: the release of sAP induced by ES0 and measured by colorimetric assay makes it possible to determine the activity of this active ingredient as a TLR2, TLR4 or TLR5 agonist.

The study was carried out on the following human embryonic kidney (HEK293) cell lines:

HEK-Blue™-2 cells for TLR2,
HEK-Blue™-4 cells for TLR4,
HEK-Blue™-5 cells for TLR5.

These cell lines are maintained in HEK-Blue™ Selection 10% FCS culture medium and then distributed in 96-well plates in HEK-Blue™ Detection medium in the presence of ES0 for 18 hours. The plates are read using calorimetry at 620 nm.

3.2.1 Activation of TLR2

Figure 6:
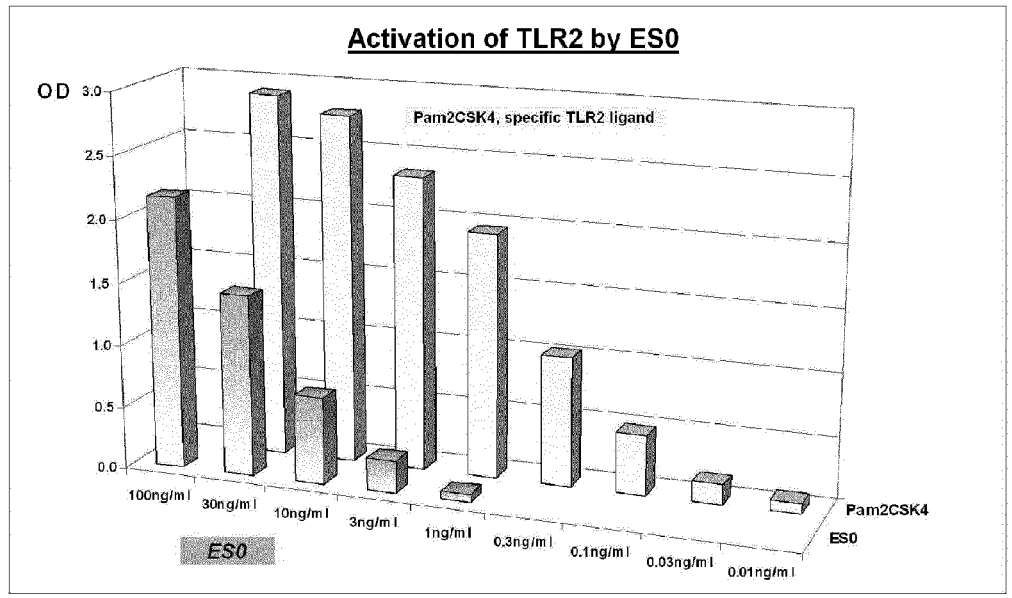
FIG. 6 illustrates activation of TLR2 by extract ES0.

Extract ES0 induces the activation of TLR2 according to a dose-dependent effect with a maximum activity at 100 ng/ml (FIG. 6).

3.2.2 Activation of TLR4

Figure 7:
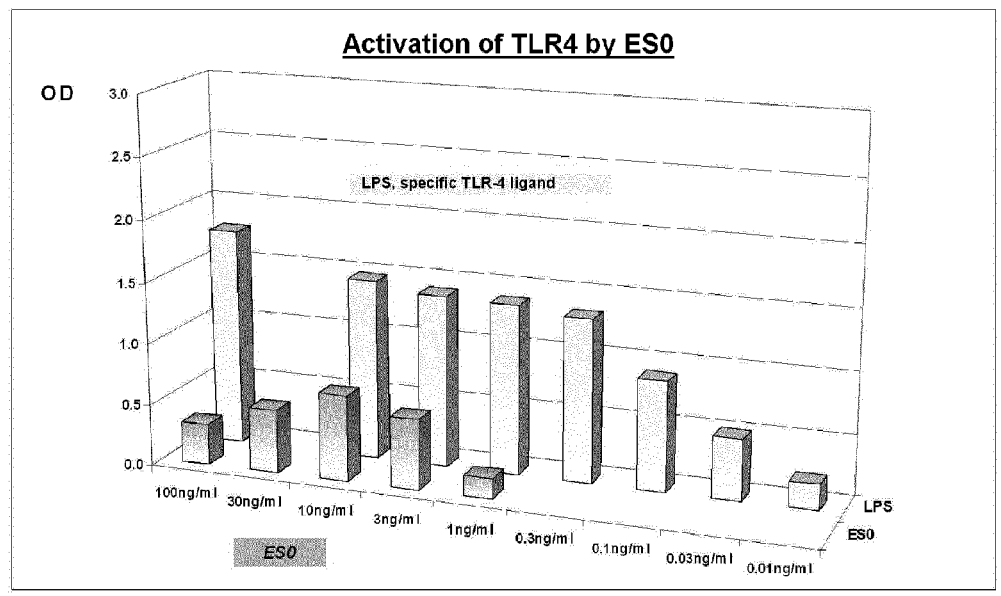
FIG. 7 illustrates activation of TLR4 by extract ES0.

Extract ES0 induces the activation of TLR4 with a maximum activity at 10 ng/ml (FIG. 7).

3.2.3 Activation of TLR5

Figure 8:
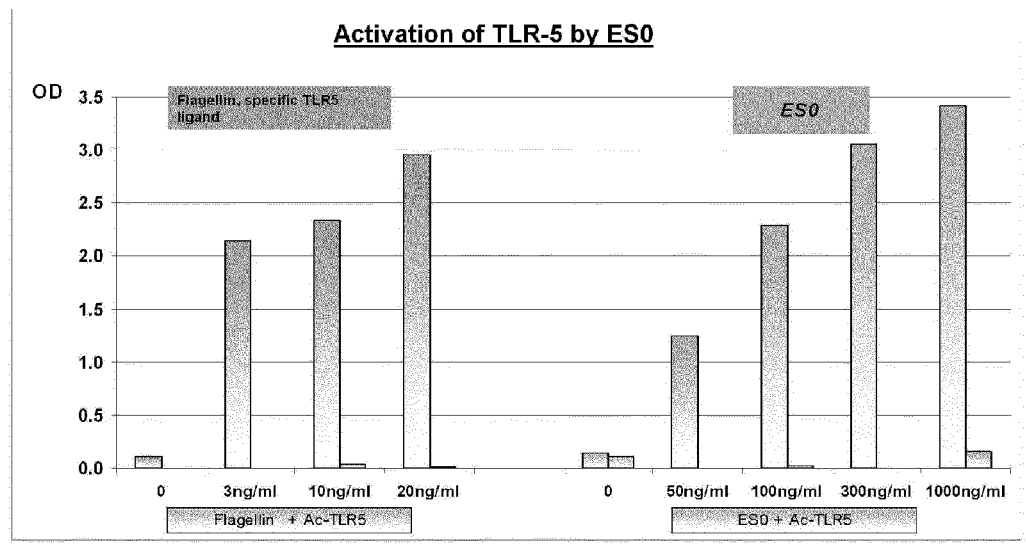
FIG. 8 illustrates activation of TLR5 by extract ES0.

Extract ES0 induces the activation of TLR5 in a dose-dependent manner. This activity is inhibited in the presence of anti-TLR5 antibody, demonstrating the activation specificity of extract ES0 on TLR5 (FIG. 8).

3.3 Inhibition of PAR2

The inhibition of protease-activated receptors by extract ES0 is evaluated on human keratinocytes from a cell line (HaCaT) by measuring the intracellular calcium influx induced after specific stimulation of PAR2 with stratum corneum tryptic enzyme (SCTE). The fluorescent probe Fluo-4/AM is used: its esterified form facilitates its penetration by passive diffusion in the cell; only the deesterified form bound to calcium ions is excitable under 485 nm fluorescence and emits at 535 nm.

The fluorescent probe is incorporated for 30 minutes in cells inoculated in 96-well plates and then extract ES0 is incubated for 30 minutes. Calcium flow is measured well by well in real time according to kinetics before and after injection of SCTE. The plates are read using a Mithras LB940™ reader (Berthold Technologies®).

Figure 9:
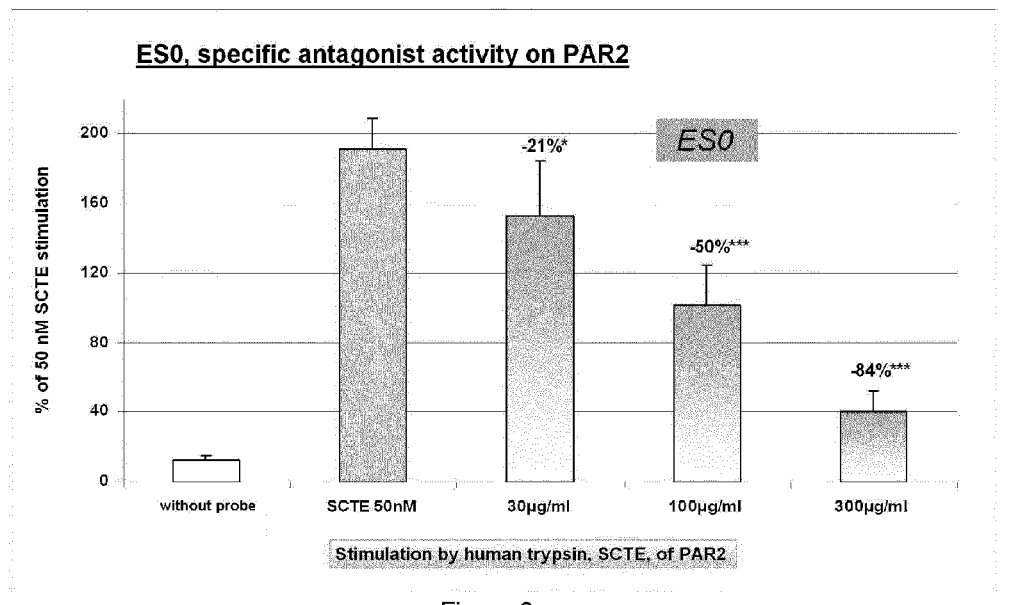
FIG. 9 illustrates specific PAR2 antagonist activity by extract ES0.

Extract ES0 inhibits in a dose-dependent manner activation of PAR2 induced by human SCTE (FIG. 9).

EXAMPLE 4

Use of Extract ES0 for the Treatment of Periodontitis

Periodontal diseases are chronic inflammatory diseases that can lead to the destruction of the periodontium. A change occurs in the bacterial flora comprising pathogenic anaerobic strains such as *Porphyromonas gingivalis* (Pg). These strains are sensitive to antimicrobial peptides which, at least for hBD-3, are found in lower quantities in the gingival crevicular fluid of subjects suffering from periodontal diseases (Brancatisano F L et al. (2011) Reduced human Beta defensin 3 in individuals with periodontal disease. J Dent Res. 90:241-245). In this experiment, we demonstrate that extract ES0 is able to induce antimicrobial peptides in oral keratinocytes.

Primary human oral keratinocytes were stimulated for 48 hours with 10 μg/ml of ES0, in the presence or the absence of 1 μg/ml of antibody specifically blocking each TLR: TLR2 (aTLR2), TLR4 (aTLR4) or TLR5 (aTLR5). Expression of the mRNA of various antimicrobial peptides (table 7 below) was quantified by real-time PCR.

TABLE 7

| GENE | PROTEIN |
| --- | --- |
| DEFB103 | hBD-3 |
| DEFB4 | hBD-2 |
| S100A7 | Psoriasin |
| RNase7 | RNase7 |

After 48 hours of stimulation, the cells were lysed and total RNA was extracted and then assayed using a NanoDrop N1000 spectrophotometer (Thermo Fisher Scientific). cDNA were synthesized from 1 μg is of RNA. The quantitative PCR amplification step was carried out using SYBR Green (SYBR Green PCR Core Reagents kit, Applied Biosystems) in 96-well plates. The DNA sequences of the primers used are presented in table 8 below.

TABLE 8

| | | |
| --- | --- | --- |
| H-DEFB103A-U | 5'-TGGGGTGAAGCCTAGCAGCTATG-3' | SEQ ID NO. 3 |
| H-DEFB103A-L | 5'-ATGATTCCTCCATGACCTGGAACA-3' | SEQ ID NO. 4 |
| H-DEFB4-U | 5'-CCATCAGCCATGAGGGTCTTGTAT-3' | SEQ ID NO. 5 |
| H-DEFB4-L | 5'-CGCCTATACCACCAAAAACACCTG-3' | SEQ ID NO. 6 |
| H-S100A7-19U | 5'-CACTCATCCTTCTACTCGTGACGC-3' | SEQ ID NO. 7 |
| H-S100A7-142L | 5'-GGCTTGGCTTCTAATCTTGTCAT-3' | SEQ ID NO. 8 |
| H-RNASE7-U | 5'-GAGTCACAGCACGAAGACCAAGC-3' | SEQ ID NO. 9 |
| H-RNASE7-L | 5'-AGCAGCAGAAGGGGGCAGAA-3' | SEQ ID NO. 10 |

The values of the cycle threshold (Ct) were normalized in relation to reference genes (GAPDH: glyceraldehyde-3-phosphate dehydrogenase; PPIA: peptidylprolyl isomerase A; YWHAZ: tyrosine 3/tryptophan5-monooxygenase; RPLP0: ribosomal protein P0). The level of expression of the gene of interest is then given in $\Delta Ct$: $\Delta Ct = Ct_{(gene\ of\ interest)} - Ct_{(reference\ gene)}$. The relative quantity (RQ) of messenger RNA for each gene of interest is calculated in relation to the corresponding untreated control cell:

$RQ = 2^{(-\Delta\Delta Ct)}$, wherein $\Delta\Delta Ct = \Delta Ct_{(treated\ cells)} - \Delta Ct_{(control\ cells)}$.

Expression of the gene of interest is considered regulated when $RQ \geq 2$ (induction) or $RQ \leq 0.5$ (inhibition).

The hBD-2 concentration in the culture supernatants was determined by ELISA using a commercial kit according to the manufacturer's recommendations (PeproTech). The results are expressed as mean±standard deviation and the percentage of inhibition of production induced, when significantly modulated, is indicated in bold blue (evaluated in relation to the production induced without antibody, "Without AB").

Figure 11:
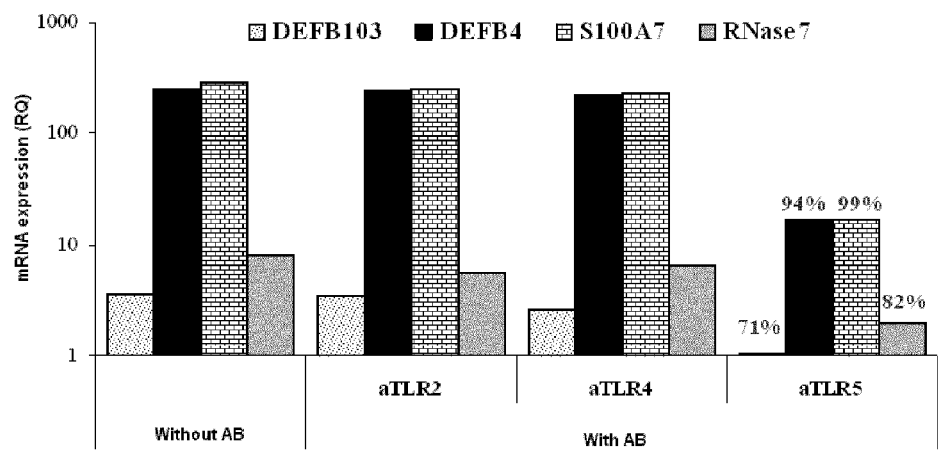
FIG. 11 demonstrates the effect of ES0 in the induction of TLR5-dependent expression of antimicrobial peptide genes.
Figure 12:
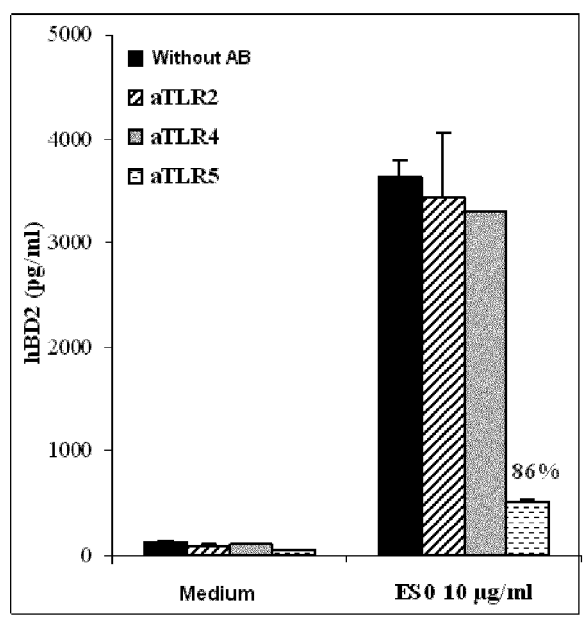
FIG. 12 illustrates that ES0 activity on human oral keratinocytes is mediated by TLR5.

The results show that ES0 is a powerful inducer of the expression of all of the antimicrobial peptides studied (FIG. 11, "Without AB"). Overexpression of the DEFB4 gene is correlated with a large increase in hBD-2 protein secretion (FIG. 12).

After pre-incubation of the cells with an anti-TLR2 or anti-TLR4 antibody, peptide expression is not affected. On the other hand, in the presence of anti-TLR5 antibody, the expression of DEFB103, DEFB4, S100A7 and RNase 7 is strongly suppressed: 71%, 94%, 99% and 82%, respectively (FIG. 11). Similarly, hBD-2 secretion is drastically reduced by 82% with anti-TLR5 antibody alone (FIG. 12).

ES0 is thus a powerful activator of antimicrobial peptide expression and secretion. This effect is related to TLR5 activation. To date, the only known TLR5 ligand is flagellin. It is thus likely that LMB64 flagellin contained in ES0 is responsible for the activation of TLR5 and the production of antimicrobial peptides.

EXAMPLE 5

Use of Extract ES0 for the Treatment of Chronic Inflammatory Bowel Disease (IBD)

The effect of ES0 was evaluated on inflammatory response in experimental colitis. The rat model of acute colitis induced by TNBS (2,4,6-trinitrobenzenesulfonic acid) is known to approximate Crohn's disease. ES0 was administered rectally to avoid its degradation during passage in the gastrointestinal tract. It is shown herein that ES0 is able to contain inflammation via inhibition of myeloperoxidase (MPO).

The effect of living bacterium LMB64 by oral route as a preventive measure was also evaluated in IBD: the effect of strain LMB64 was evaluated in the rat model of acute colitis induced by TNBS. Living strain LMB64 was administered by oral route.

5.1 Extract ES0

The effect of ES0 was evaluated on inflammatory response in experimental colitis. The rat model of acute colitis induced by TNBS (2,4,6-trinitrobenzenesulfonic acid) is known to approximate Crohn's disease. ES0 was administered rectally to avoid its degradation during passage in the gastrointestinal tract.

Groups of 10 Wistar rats received 30 mg of TNBS rectally at D0. Various doses of ES0 (7.5, 0.75 and 0.075 mg of proteins/kg) were administered daily from D0 to D6. The animals were sacrificed at D7 to determine the local inflammatory reaction by assaying the enzyme myeloperoxidase (MPO) present in neutrophils. Briefly, a section of colon was homogenized and MPO activity was quantified by spectrophotometric assay in the supernatant.

The results are expressed as mean±standard deviation.

A statistical analysis of the data was carried out using a one-way ANOVA followed by a Bonferroni test.

Figure 13:
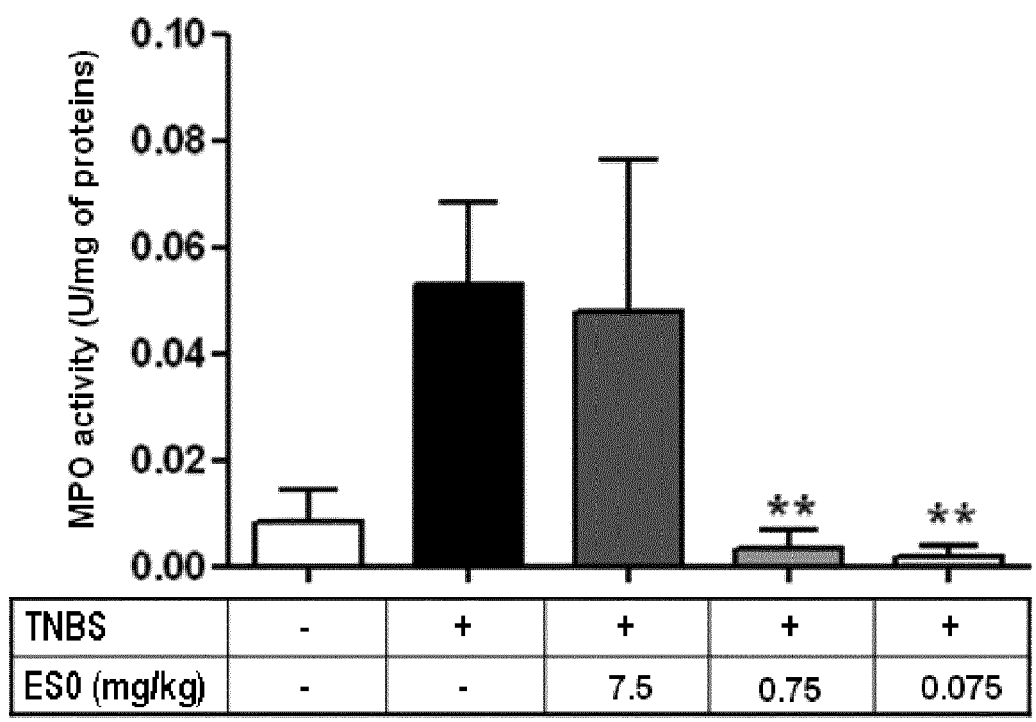
FIG. 13 illustrates the anti-inflammatory effect of ES0 in a model of acute colitis in the rat.

The administration of TNBS induces a significant increase in activity in relation to the untreated control group. In rats receiving ES0 at doses of 0.75 mg/kg or 0.075 mg/kg, but not at the strongest dose, MPO activity is significantly inhibited compared to the TNBS-treated positive control group. The effect of ES0 is powerful since MPO activity returns to normal, i.e., similar to that of the negative control group not treated with TNBS (FIG. 13).

5.2 Bacterium LMB64 as a Preventive Measure in Chronic Inflammatory Bowel Disease The effect of strain LMB64 was evaluated in the rat model of acute colitis induced by TNBS. The LMB64 culture was centrifuged and washed with physiological buffer. The bacterium is resuspended in 0.9% NaCl physiological buffer. The solution titrated in number of bacteria LMB64 was administered to the animal by oral route.

Groups of 10 Wistar rats received 30 mg of TNBS rectally at D0. Various doses of LMB64 ($10^8$ or $10^9$ living bacteria) were administered daily from D-6 to D0. A group of rats receiving 3 mg/kg of prednisolone, used as a reference molecule and according to the same protocol, was also included. The animals were sacrificed at D7.

Macroscopic lesions were evaluated and expressed according to a score based on the parameters described in table 9 below.

TABLE 9

| Parameter | Score |
|---|---|
| Normal appearance | 0 |
| Local bleeding, no ulcer | 1 |
| Ulceration without bleeding or thickening of the intestinal wall | 2 |
| Ulceration with a site of inflammation | 3 |
| Ulceration with two or more sites of inflammation | 4 |

Local inflammatory reaction was determined by MPO assay as described above.

The results are expressed as mean±standard deviation. A statistical analysis of the data was carried out using a one-way ANOVA followed by a Bonferroni test.

Figure 14A:
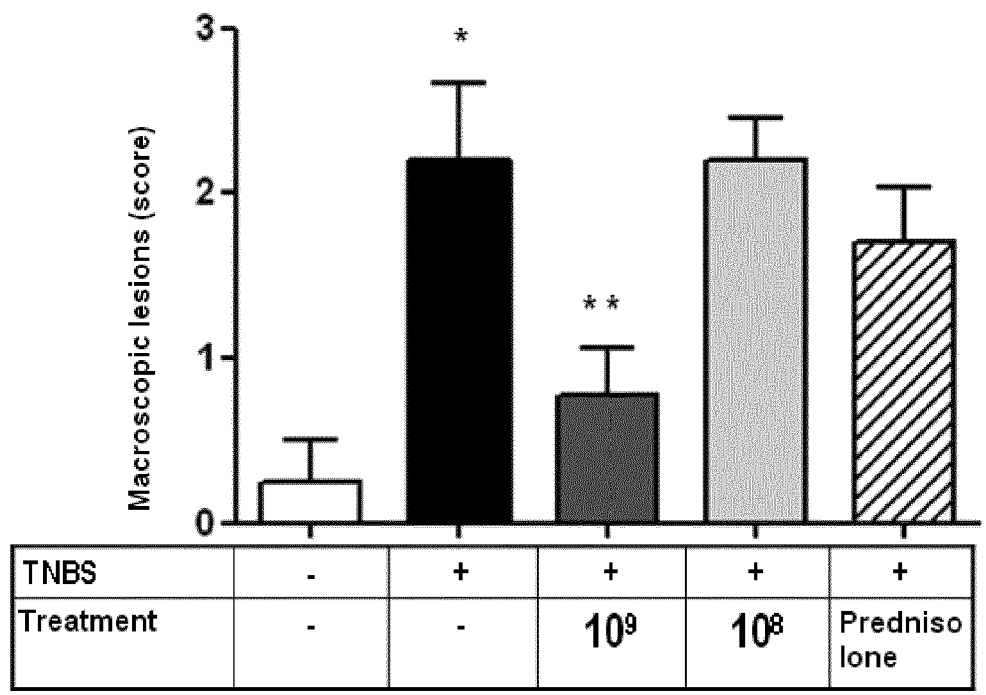
FIGS. 14A and 14B demonstrate that strain LMB64 administered preventatively significantly reduces intestinal lesions induced by TNBS [A] as well as the inflammatory response (MPO activity) [B].
Figure 14B:
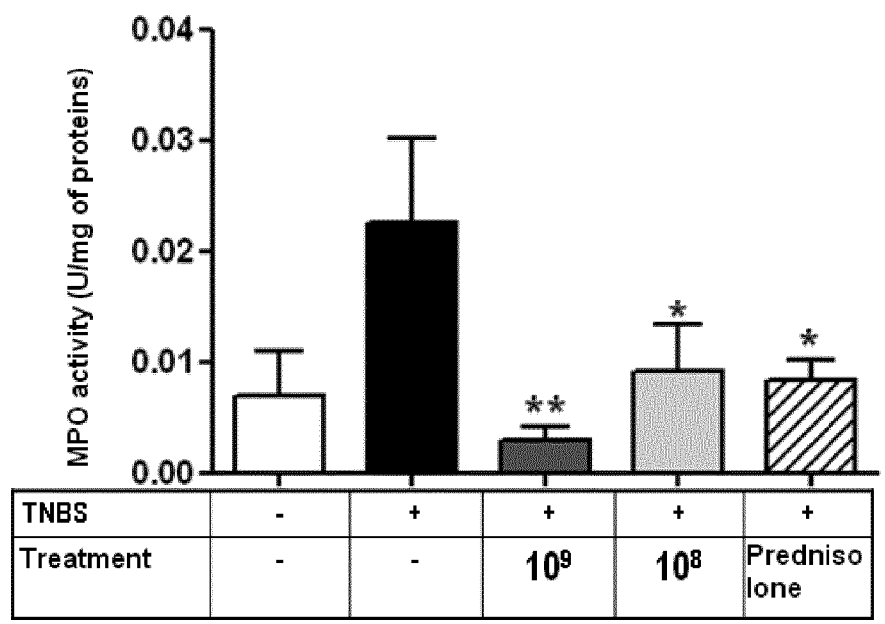

The results show that LMB64, in a surprising manner, inhibits the inflammatory reaction as expressed by MPO activity (FIG. 14B). This effect is dose-dependent, wherein maximum activity is obtained with $10^9$ bacteria LMB64.

At this dose, strain LMB64 is more effective than the reference molecule, prednisolone. LMB64 is also able to drastically reduce the lesion score, but only at a dose of $10^9$ bacteria LMB64 (FIG. 14A). Again, the strain proves more effective than the reference molecule, prednisolone.

The invention claimed is:

1. A composition comprising a bacterial extract as an active ingredient and a pharmaceutically acceptable carrier,
   wherein the bacterial extract is obtained from a suspension of bacteria, and
   wherein said bacteria of the suspension is a nonpathogenic Gram-negative bacterium belonging to the class Betaproteobacteria, subfamily Neisseriaceae, and characterized in that a nucleotide sequence of a 16S rRNA gene of said bacterium includes sequence SEQ ID NO: 1.

2. The composition according to claim 1, wherein said bacterium of the bacterial extract is the bacterium deposited with the CNCM on Apr. 8, 2010, under the reference 1-4290.

3. Bacterial extract obtained from a suspension of bacteria,
   wherein said bacteria of the suspension is a nonpathogenic Gram-negative bacterium belonging to the class Betaproteobacteria, subfamily Neisseriaceae, and characterized in that a nucleotide sequence of a 16S rRNA gene of said bacterium includes sequence SEQ ID NO: 1, and wherein the bacterial extract is obtained after treatment of said bacterial suspension in such a way as to eliminate intracellular components.

4. Bacterial extract according to claim 3, wherein said intracellular components include at least nucleic acids.

5. Bacterial extract according to claim 3, wherein it includes a fraction E0 comprising at least membrane proteins, periplasmic proteins and proteins arising from the flagellum.

6. Bacterial extract according to claim 5, wherein said membrane proteins consist of porins, OmpA, lipopolysaccharides and/or lipoproteins.

7. Bacterial extract according to claim 3, wherein it includes a fraction SO comprising at least secreted peptides and proteins and secondary metabolites.

8. Bacterial extract according to claim 3, wherein it includes a fraction ESO comprising at least fraction E0 and fraction SO.

9. Bacterial extract according to claim 8, wherein said fraction ESO has a protein profile, obtained by SDS-PAGE, which includes three principal bands corresponding to molecular weights ranging between 30 kDa and 36 kDa, 41 kDa and 45 kDa, and 47 kDa and 51 kDa, respectively.

10. Composition comprising at least, as an active ingredient, a bacterial extract according to claim 3.

11. Composition according to claim 10, for the treatment of gastrointestinal and oral inflammatory diseases.

12. Composition according to claim 11, wherein said gastrointestinal and oral inflammatory diseases consist of Crohn's disease, colitis or periodontitis.

13. Composition according claim 10, wherein further comprising a pharmaceutically acceptable carrier.

14. Method of activating TLR2, TLR4 and/or TLR5 which comprises contacting cells expressing TLR2, TLR4 and/or TLR5 with a bacterial extract of claim 1.

15. Method of inhibiting PAR2 activation, which comprises contacting cells expressing PAR2 with a bacterial extract of claim 7.

* * * * *